(12) United States Patent
Orion et al.

(10) Patent No.: US 10,004,508 B2
(45) Date of Patent: Jun. 26, 2018

(54) VESSEL SHAPING DEVICES AND METHODS

(75) Inventors: Eyal Orion, Ramat Efal (IL); Tamar Gilon, Tel Aviv (IL)

(73) Assignee: LAMINATE MEDICAL TECHNOLOGIES LTD., Tel Aviv (IL)

( * ) Notice: Subject to any disclaimer, the term of this patent is extended or adjusted under 35 U.S.C. 154(b) by 438 days.

(21) Appl. No.: 14/236,635

(22) PCT Filed: Aug. 1, 2012

(86) PCT No.: PCT/EP2012/065078
§ 371 (c)(1),
(2), (4) Date: Mar. 24, 2014

(87) PCT Pub. No.: WO2013/017639
PCT Pub. Date: Feb. 7, 2013

(65) Prior Publication Data
US 2014/0194910 A1 Jul. 10, 2014

Related U.S. Application Data

(60) Provisional application No. 61/513,976, filed on Aug. 1, 2011.

(51) Int. Cl.
*A61B 17/11* (2006.01)
*A61M 1/36* (2006.01)
(Continued)

(52) U.S. Cl.
CPC ............... *A61B 17/11* (2013.01); *A61F 2/82* (2013.01); *A61M 1/3655* (2013.01); *A61F 2002/068* (2013.01)

(58) Field of Classification Search
CPC ........ A61M 1/3655; A61M 1/36; A61M 1/14; A61F 2002/068; A61F 2/82; A61F 2/06;
(Continued)

(56) References Cited

U.S. PATENT DOCUMENTS

| 5,968,089 A | 10/1999 | Krajicek |
| 6,071,306 A | 6/2000 | Angelini |

(Continued)

FOREIGN PATENT DOCUMENTS

| CN | 2394583 | 9/2000 |
| CN | 2526019 | 12/2002 |

(Continued)

OTHER PUBLICATIONS

International Search Report for PCT/EP2012/065078 dated Nov. 7, 2012.
(Continued)

*Primary Examiner* — Christopher L Templeton
*Assistant Examiner* — George J Ulsh
(74) *Attorney, Agent, or Firm* — A.C. Entis-IP Ltd.

(57) ABSTRACT

Disclosed is a medical device for shaping a vessel accommodated therein in a predetermined form, wherein said vessel includes a vein and an artery which are connected at a artifactual vascular junction thereof. The device includes an external vascular support (100) having at least one vascular support wall for accommodating an exterior vessel wall of a vessel therein when implanted. The support includes an arterial portion (1304) for apposition with said artery when accommodated therein, and/or a venous portion (1302) for apposition with said vein when accommodated therein. The venous portion (1302) and/or said arterial portion (1304) are shaped at a junction thereof to provide a vessel rounding to at least a portion of said vessel junction when in apposition with the latter upon implantation of said device for said vessel shaping. Corresponding methods are also disclosed. Thus dysfunction or failure of a vessel of the artifactual vascular junction may be reduced, minimized, or eliminated.

15 Claims, 16 Drawing Sheets

(51) Int. Cl.
*A61F 2/82* (2013.01)
*A61F 2/06* (2013.01)

(58) Field of Classification Search
CPC . A61B 17/11; A61B 17/12; A61B 2017/1107; A61B 2017/1135; A61B 17/1114
USPC ............ 604/8; 606/152, 153, 156, 158
See application file for complete search history.

(56) References Cited

U.S. PATENT DOCUMENTS

| | | | |
|---|---|---|---|
| 2002/0173809 A1 | 11/2002 | Fleischman et al. | |
| 2003/0229365 A1 | 12/2003 | Whayne et al. | |
| 2004/0097988 A1 | 5/2004 | Gittings et al. | |
| 2005/0261713 A1 | 11/2005 | Hassan et al. | |
| 2006/0282106 A1 | 12/2006 | Cole et al. | |
| 2008/0195124 A1 | 8/2008 | Borghi | |
| 2008/0294245 A1* | 11/2008 | Lundh ............... | A61F 2/06 623/1.35 |
| 2008/0305999 A1* | 12/2008 | Martin ............... | A61K 48/005 514/7.4 |
| 2009/0024208 A1 | 1/2009 | Barker | |
| 2009/0076531 A1* | 3/2009 | Richardson ......... | A61F 2/064 606/153 |
| 2010/0204783 A1 | 8/2010 | Nugent et al. | |
| 2011/0230955 A1* | 9/2011 | Orion ................. | A61F 2/82 623/1.15 |
| 2012/0071965 A1 | 3/2012 | Longo et al. | |
| 2012/0123451 A1 | 5/2012 | Asfora et al. | |

FOREIGN PATENT DOCUMENTS

| | | |
|---|---|---|
| CN | 102307542 | 1/2012 |
| DE | 10205997 | 9/2003 |
| GB | 2344053 | 5/2000 |
| JP | 2003504166 | 2/2003 |
| JP | 2008522735 | 6/2006 |
| WO | 2010058406 | 5/2010 |
| WO | 20110161493 | 5/2011 |

OTHER PUBLICATIONS

Japanese Office Action dated May 23, 2016 for application No. 2014-523323 filed Feb. 3, 2014.
Roy-Chaudhury, Prabir et al.; Vascular Access in Hemodialysis: Issues, Management, and Emerging Concepts; Cardiology Clinics, vol. 23; published 2005; pp. 249-273.
International Search Report dated Nov. 4, 2013 for PCT Application No. PCT/IB2013/056322 filed Aug. 1, 2013.
Office Action dated Dec. 2, 2016 for European Application No. 12743153.4, filed Feb. 28, 2014.
U.S. Office Action dated May 20, 2016 for corresponding U.S. Appl. No. 14/611,256, filed Feb. 1, 2015.
U.S. Office Action dated Jun. 4, 2015 for corresponding U.S. Appl. No. 14/611,256, filed Feb. 1, 2015.
U.S. Final Office Action dated Nov. 16, 2016 for corresponding U.S. Appl. No. 14/611,256, filed Feb. 1, 2015.
U.S. Final Office Action dated Dec. 2, 2015 for corresponding U.S. Appl. No. 14/611,256, filed Feb. 1, 2015.
European Office Action dated Aug. 18, 2015 for corresponding Application No. 13762280.9, filed Feb. 27, 2015.
Chinese Office Action dated Nov. 8, 2016 for corresponding Application No. 2013800516184, filed Jan. 30, 2015.
Chinese Office Action dated Mar. 21, 2016 for corresponding Application No. 2013800516184, filed Jan. 30, 2015.
Canadian Office Action dated Dec. 21, 2015 for corresponding Application No. 2880343, filed Jan. 28, 2015.
Australian Office Action dated Nov. 14, 2016 for corresponding Application No. 2013298145, filed Mar. 2, 2015.
International Preliminary Report on Patentability dated Nov. 25, 2014 for PCT Application No. PCT/IB2013/056322 filed Aug. 1, 2013.
Office Action dated Mar. 20, 2017 for Japanese Application No. 2014-523323, filed Feb. 3, 2014.
U.S. Final Office Action dated Nov. 27, 2017 for corresponding U.S. Appl. No. 14/611,256, filed Feb. 1, 2015.

\* cited by examiner

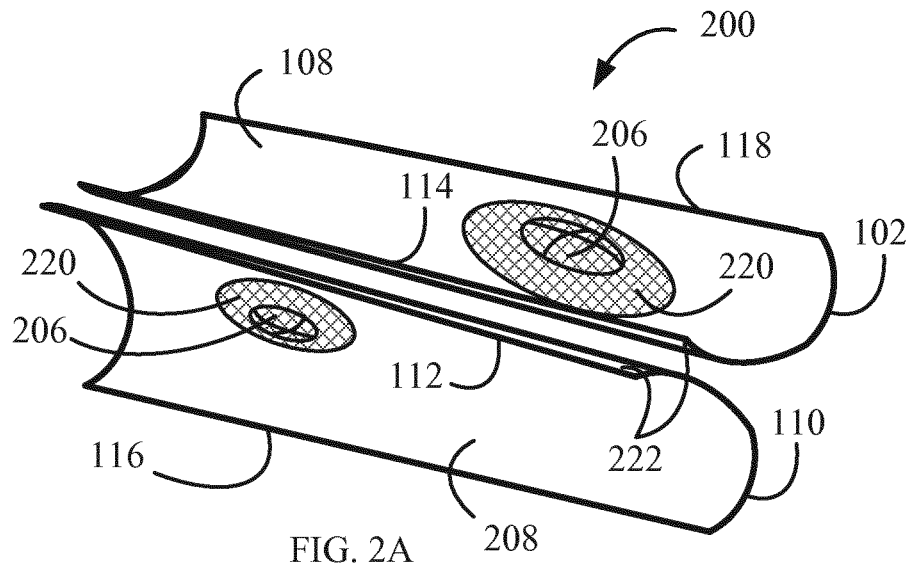
FIG. 2A
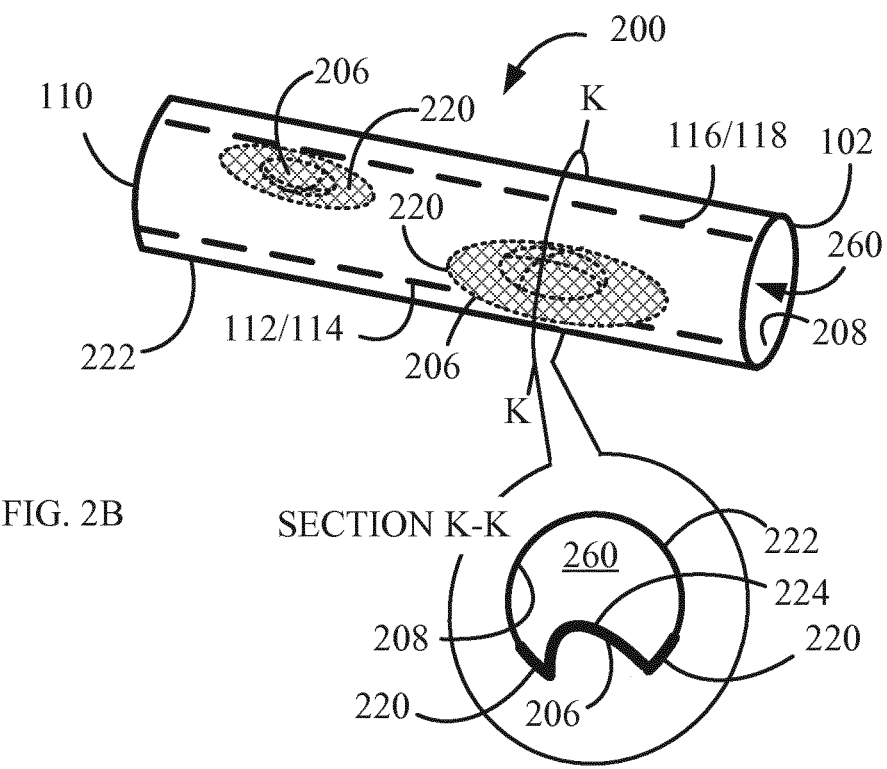
FIG. 2B   SECTION K-K

VESSEL SHAPING DEVICES AND METHODS

RELATED APPLICATIONS

The present application is a U.S. National Phase of PCT Application No. PCT/EP2012/065078, filed on Aug. 1, 2012, which claims benefit under 35 U.S.C. 119(e) from U.S. Provisional Application No. 61/513,976, filed Aug. 1, 2011. The contents and disclosures of these prior applications are incorporated herein by reference in their entirety.

TECHNICAL FIELD

The disclosed method and apparatus relate to devices for shaping body lumen, and more particularly the disclosure pertains to external vessel shaping devices such as for externally modifying a body liquid flow inside the vessel.

BACKGROUND

At normal conditions, blood flows in large conduits of the vascular system (i.e., veins and arteries) in an unhindered non-turbulent manner. On some occasions, for example during vascular related illness or after surgery, a local change to blood vessel cross section and/or an introduction of a new opening along its periphery (e.g., as result of a bypassing graft), will cause an immediate change to the original local flow regime, thereby creating "stagnant areas" in which pressures are substantially low and flow is minimal or even absent, and/or "turbulent areas" in which pressures are substantially high and turbulent flow occurs. A healthy vessel will then undergo a prolonged process of local remodeling and/or reshaping that in some circumstances will lead to severe cases of vessel obstruction and/or organ failure.

In surgical jargon, an anastomosis commonly relates to the joining together of two hollow organs, such as a vein to an artery. Anastomoses may be performed end-to-end, side-to-side or end-to-side depending on the circumstances of the required reconstruction or bypass. Anastomoses are typically performed on arteries and veins, including most vascular procedures such as all arterial bypass operations (e.g. coronary artery bypass). Patients with end stage renal disease undergo frequent hemodialysis to remove toxins from the blood and maintain appropriate homeostasis. In dialysis, blood is withdrawn from a vascular access, purified, and returned to a vein or a synthetic graft.

The most common form designed to enable long-term vascular access in chronic hemodialysis patients is the native arteriovenous (AV) fistula.

In the AV fistula method, openings are created in an artery and vein, usually in the arm above or below the elbow. The borders of the openings are attached, to create a fistula. The arterial blood pressure, being higher than the venous pressure, together with the supra-physiological flow rates, eventually enlarges the vein and a "mature" and a functioning vascular access is created 2-4 months post procedure. The mature vascular access enables sufficient blood flow rate, effective dialysis procedure and the accommodation of a cannula or large needles.

Hemodialysis vascular access dysfunction is the single most important cause of morbidity in the hemodialysis. According to Roy-Chaudhury et al., "Vascular access in hemodialysis: issues, management, and emerging concepts" (in Cardiology Clinics 23, 2005: 249-223) there are several causes of failures of vascular access procedures.

In the AV fistula Roy-Chaudhury et al. identify the two main causes of such failure as being early maturation failure and late venous stenosis, both caused by neointimal hyperplasia.

Early maturation failure is usually caused by the development of a juxta-anastomotic stenosis due to neointimal hyperplasia in propinquity to the artery-vein anastomosis.

Hence, there is a need for an advantageous method and/or apparatus for alleviating, or preventing anastomotic dysfunction or failure.

It may be desired to reduce, minimize or prevent the buildup of neointimal hyperplasia. It may alternatively or in addition be desired to reduce, minimize or prevent vascular constriction and/or luminal stenosis, e.g. resulting from neointimal hyperplasia.

It may alternatively or in addition be desired in certain cases to prevent, minimize or eliminate hemodialysis vascular access dysfunction.

SUMMARY

The inventors of the present disclosure perceived that it may be advantageous to perform favorable remodeling adjacent vascular access anastomosis in order to affect local flow regime in the effort to diminish or prevent local failure, such as the occurrence of luminal stenosis.

The inventors of the present disclosure have realized that modification of the flow regime within a vessel may diminish or even eliminate areas of flow stagnation or turbulence and prevent the ill-effects such occurrences may have on the vessel. This in turn may prevent anastomotic dysfunction or failure.

Consequently, it may be an advantageous solution to have a medical device, which can effectively change the characteristics of the flow in the vicinity of an anastomosis, optionally an end-to-side anastomosis designed for flow from the "side portion" (i.e., the arterial member) to the "end portion" (i.e., the venous member). It may further be advantageous to have a medical device, which also comprises a vascular support. In addition, it may be advantageous to have a medical device for affecting a permanent change to a local flow regime in a vessel.

The present method and/or apparatus provide an external vascular support designed to modify a flow regime within a single vessel, one or more vessels or an anastomosis or a junction of vessels. The disclosed method and apparatus are for instance provided to diminish or eliminate unfavorable remodeling of the vessels. Such remodeling may for instance result from neointimal hyperplasia, vascular constriction and/or luminal stenosis, which are reduced, minimized or prevented by examples of the disclosure.

Some examples of the present device and procedure provide an external vascular support designed to prevent, minimize or eliminate hemodialysis vascular access dysfunction.

According to one aspect of the invention, a medical device for shaping a vessel accommodated therein in a predetermined form, the vessel comprising a vein and an artery which are connected at an artifactual vascular junction thereof, is provided. The device comprises an external vascular support having at least one vascular support wall for accommodating an exterior vessel wall of a vessel therein when implanted. The vascular support has an arterial portion for apposition with the artery when accommodated therein. Alternatively or in addition aid vascular support has a venous portion for apposition with the vein when accommodated therein. The arterial portion and/or the venous portion are shaped at the vascular junction to provide a vessel rounding of the vascular junction when in apposition with the vascular junction upon implantation of the device for the vessel shaping. The vessel rounding is provided to at least a portion of the vascular junction or an immediate vicinity thereof. Preferably, the vessel rounding is provided at an inflow side of the vascular junction as a junction rounding.

According to another aspect of the invention, a medical procedure for affecting dysfunction or failure of a vessel of an artifactual vascular junction is provided. The procedure includes providing a medical device for shaping at least the vessel when accommodated therein in a predetermined form. The vessel comprises a vein and an artery which are connected at the artifactual vascular junction thereof. implanting the device at and/or in the vicinity of the artifactual vascular junction, Furthermore, the procedure includes arranging a vascular support of the device external to the vessel by accommodating an exterior vessel wall of the vessel therein. Moreover, the procedure includes bringing an arterial portion of the vascular support in apposition with the artery when accommodated therein. Alternatively or in addition, the procedure includes bringing a venous portion of the vascular support in apposition with the vein when accommodated therein. In addition, the procedure includes shaping the vascular junction by the venous portion and/or the arterial portion and thereby providing a vessel rounding to at least a portion of the vascular junction, or an immediate vicinity thereof, which is in apposition with the implanted device.

According to yet another aspect of the invention, a medical procedure for affecting anastomotic dysfunction or failure is provided. The procedure includes shaping an artifactual vascular junction of an artery and a vein in an end-to-side anastomosis at the vascular junction with a permanent rounding to at least a portion of the vessel junction.

According to a further aspect of the invention, a medical device is provided. The medical device comprises a vascular support having at least one vascular support wall for accommodating a vessel wall of a vessel. The medical device further comprises at least one flow modifying component protruding from the vascular support wall for affecting a permanent change to a local flow regime in the vessel when the flow modifying component is in apposition with the vessel. The at least one flow modifying component preferably protrudes from the vascular support towards the vessel wall. The at least one flow modifying component has a predetermined tridimensional shape operative to modify the local flow regime, including a rounding with at least one radius of defined curvature.

According to a further aspect of the invention, a flow modifying component for external apposition to a vessel of an artifactual junction of vessels is provided. The flow modifying component has a predetermined tridimensional shape for affecting a change to a local flow regime in the vessel for preventing dysfunction or failure of the anastomosis, when the flow modifying component is in apposition with the vessel. The tridimensional shape includes a rounding.

Further embodiments of the invention are defined in the dependent claims, wherein features for the second and subsequent aspects of the invention are as for the first aspect mutatis mutandis.

There is thus provided, in accordance with an exemplary examples of the current method and apparatus, an apparatus for external vascular support including one or more vessel accommodating portions. The one or more vessel accommodating portions may include one or more walls having a concave surface defining a trough. Further, they may comprise a cover portion fitted so that when attached, both portions enclose one or more vessels accommodated in one or more lumens of the apparatus defined between the attached portions or by each of the portions separately. One or more flow modifying elements may protrude into the lumen from the internal wall of one or more of the portions. When in apposition with a vessel in the lumen, the vessel lumen may thus be modified for modification of a liquid flow therein. In some examples, at least some of the flow modifying elements may be considered or defined as "hemodynamic shaped" or "hydrodynamic shaped" elements in the sense that they include a tridimensional shape and/or a two-dimensional cross-section suited for diminishing local turbulence (e.g., incorporating a chosen small or minimal drag coefficient).

In accordance with another example of the present disclosed method and apparatus, there is also provided an apparatus for external vascular support including one or more plastically formable segments at pre-determined locations. The formable segments may be button-shaped or wing-shaped and operative to be pressed creating invaginations in the support internal wall, formed into flow modifying elements protruding into a lumen of a vessel.

In accordance with yet another example of a disclosed method and apparatus, there is also provided an apparatus for external vascular support in which the support as a whole, may be plastically formable and may be shaped and molded in real time as desired to modify a flow regime within a vessel.

In accordance with still another example of the presently disclosed method and apparatus, there is also provided an apparatus for external vascular support having an expandable flow modifying element.

In accordance with another example of the presently disclosed method and apparatus, there is also provided an apparatus for external vascular support including at least two portions intersecting at an angle smaller than 90 degrees defining at least two lumens therebetween operative to accommodate an anastomosis of at least two vessels.

In accordance with yet another example of the presently disclosed method and apparatus, there is also provided an apparatus for external vascular support including one or more portions intersecting at an angle ($\alpha$) equal to or smaller than 90 degrees and also including a plastically deformable portion enveloping the junction of the one or more intersecting portions.

In accordance with still another example of the presently disclosed method and apparatus, there is also provided an apparatus for external vascular support including at least two portions intersecting at an angle smaller than 90 degrees and having a flow modifying element operative to round an acute angle at the junction of the intersecting portions.

In accordance with another example of the presently disclosed method and apparatus, there is also provided an apparatus for external vascular support including a venous portion that may be longer than a host artery portion. The venous portion may be conical in shape.

In accordance with yet another example of the presently disclosed method and apparatus, there is also provided an apparatus for external vascular support including one or more sensors attached to at least one of an internal and external walls of the support, the output signals of which carried by a wire or remotely to a controller.

In accordance with an example of the disclosure, a system is provided for modifying flow in a vessel. The system includes a unit for identifying locations and dimensions of regions of low shear stress and turbulence in said vessel; a unit for analyzing said regions of low shear stress and turbulence; and a unit for selecting a tridimensional flow modifying component shape known to at least diminish said regions of low shear stress and turbulence based on said analysis.

In accordance with an example of the disclosure, a system is provided for modifying flow in a vessel. The system includes a unit for externally modifying a wall of said vessel at at least one location, such as corresponding to at least one of said regions in said selected shape thereby diminishing or eliminating at least one of said regions of low shear stress and turbulence.

In accordance with an example of the disclosure, a system is provided for affecting or preventing failure of an arteriovenous anastomosis vascular access procedure. The system may include the system of one or both of the previous paragraphs. The system may include a unit for identifying locations and dimensions of regions of low shear stress and turbulence in anastomosed vessels flow regime; a unit for analyzing said regions of low shear stress and turbulence; a unit for applying a template or support including at least one selected tridimensional flow modifying component having a shape known to at least diminish said regions of low shear stress and turbulence based on said analysis; and optionally a unit for evaluating the effect of said flow modifying component on said flow regime; and a unit for replacing said template with a selected pre-manufactured vascular support or externally adjusting said support modification as necessary to diminish or eliminate at least one of said regions of low shear stress and turbulence.

In accordance with an example of the disclosure, a system is provided for affecting or preventing failure of an arteriovenous anastomosis vascular access procedure. The system may include the system of the previous paragraph. The system includes a unit for externally modifying at least one wall of said anastomosed vessels at at least one location corresponding to at least one of regions, such as regions of low shear stress and turbulence. The system may further include a pre-manufactured vascular support for externally adjusting said support modification as necessary to diminish or eliminate at least one of said regions of low shear stress and turbulence.

In accordance with an example of the disclosure, the venous portion and/or the arterial portion have a corresponding rounding to the vessel rounding at least on their inside wall at the junction.

In accordance with an example of the disclosure, the arterial portion and the venous portion are at least partially embracing the artery and vein respectively, when implanted, and shaped to provide the rounding both at a venous segment and an arterial segment at the junction upon implantation of the device for the vessel shaping.

In accordance with an example of the disclosure, the vessel rounding is provided to obtain a substantially laminar flow in the vessel, at least in the vein downstream the vascular junction having the vessel rounding, and/or to minimize or eliminate zones of the vessel associated with low shear stress and turbulence.

In accordance with an example of the disclosure, the artifactual vascular junction is made by an end-to-side anastomosis. The arterial portion and/or the venous portion are configured to embrace the artery and vein respectively, when implanted. The device is shaped for arranging the venous portion relative the arterial portion at an angle. The venous portion and the arterial portion are preferably joined together so as to fixedly define the angle. The angle is preferably smaller than or equal to 90 degrees at the vascular junction.

In accordance with an example of the disclosure, the venous portion and the arterial portion are arranged with an acute angle at a first junction portion of the junction and an obtuse angle at an opposite second junction portion of the junction. The vascular support comprises the rounding at the first portion having the acute angle.

In accordance with an example of the disclosure, the acute angle is in the range of 20 to 60 degrees.

In accordance with an example of the disclosure, the venous portion is configured to embrace the vein when implanted, and has at least partly a frustum shape, such as including a truncated conical shape, with a smallest diameter adjacent the junction.

In accordance with an example of the disclosure, the medical device includes at least one flow modifying component, that preferably protrudes from the device to the exterior vessel wall of the vessel. The flow modifying component has a predetermined tridimensional shape operative to modify a local flow regime in the vessel, preferably for dampening or diminishing a local turbulence in the vicinity of a location of the vessel in apposition with the flow modifying component upon implantation of the device In accordance with an example of the disclosure, the shape of the at least one flow modifying component includes a rounding that has a curvature for providing the vessel junction with a vessel rounding of corresponding shape and size when in apposition with the rounding of the flow modifying component.

In accordance with an example of the disclosure, the venous portion has a greater length than the arterial portion. The venous portion has preferably a length in the range between 1 and 6 cm, particularly in the range between 2 and 3 cm.

In accordance with an example of the disclosure, the vascular support includes at least one formable portion at the junction operative to enable spatial manipulation of the arterial portion relative to the venous portion, and/or at least one formable portion at the junction operative to enable spatial manipulation of the venous portion relative to the artery portion.

In accordance with an example of the disclosure, the vascular support is rigid, semi-rigid, or elastic.

In accordance with an example of the disclosure, the vascular support is at least one of restrictive, constrictive, loosely overlaying and elastically radially expandable to a predetermined limit, in at least one of the venous portion and the artery portion.

In accordance with an example of the disclosure, the vascular support is expansible for allowing vessel expansion up to a limit at which vessel walls are restricted to acquire the shape of internal walls of the vascular support.

In accordance with an example of the disclosure, the vascular support has a shape, when implanted, that narrows segments of a vessel therein for forcing the vessel to acquire a predetermined shape including the rounding.

In accordance with an example of the disclosure, the venous portion and/or arterial portion are bendable for conforming to a vessel shape.

In accordance with an example of the disclosure, the walls of the vascular support are at least one of porous or a mesh so as to allow tissue growth into and through the walls of the vascular support over time.

In accordance with an example of the disclosure, the vascular support wall includes a concave surface defining a trough.

In accordance with an example of the disclosure, the venous portion has a single lumen deployable over the vein.

In accordance with an example of the disclosure, at least one anchoring unit, such as a suture, for anchoring the device in place once deployed is provided in an aggregate with the medical device.

In accordance with an example of the disclosure, at least a first anchoring unit of the anchoring units is applied to the venous portion once it is deployed over the vein.

In accordance with an example of the disclosure, at least a second anchoring unit of the anchoring units is applied to the arterial portion once it is deployed over the artery, optionally in front of the junction.

In accordance with an example of the disclosure, the anchoring unit includes a brace unit.

In accordance with an example of the disclosure, at least one of the anchoring units includes at least one flow modifying component that protrudes from the device to the exterior vessel wall of the vessel, having a predetermined tridimensional shape operative to modify a local flow regime in the vessel, in particular the artery.

In accordance with an example of the disclosure, the artifactual junction is an end-to-side anastomosis at a vascular junction of the artery and the vein.

In accordance with an example of the disclosure, the external vascular support includes a mold for the vessel.

In accordance with an example of the disclosure, a system for affecting failure of an arteriovenous anastomosis procedure is provided. The system includes the medical device. The system further includes a vascular support unit for externally modifying at least one wall of anastomosed vessels at at least one location corresponding to a region of low shear stress and turbulence in anastomosed vessels flow regime. The unit includes at least one selected tridimensional flow modifying component having a shape known to at least diminish the regions of low shear stress and turbulence. In this example, the vascular support unit of the system is the external vascular support of the device.

In accordance with an example of the disclosure, the procedure includes creating an arteriovenous fistula or an arteriovenous shunt, for hemodialysis, e.g. when said artifactual junction is an end-to-side anastomosis at a vascular junction of said artery and said vein.

Some embodiments provide for more uniform substantially laminar flow.

Some embodiments also provide for reduction, minimization or elimination of turbulent flow.

Some embodiments also provide for that a vessel is forced to acquire a predetermined shape.

Some embodiments also provide for that vascular access procedure failures can be reduced, minimized or eliminated.

Some embodiments also provide for increased support of or for securing the positioning of the medical device.

BRIEF DESCRIPTION OF THE DRAWINGS

The present disclosure will be understood and appreciated more fully from the following detailed description, taken in conjunction with the drawings in which:

FIGS. 2A, 2B and 2C are elevated oblique and cross-section view simplified illustrations of other exemplary embodiments in accordance with the current method and apparatus;

GLOSSARY

Figure 1A:
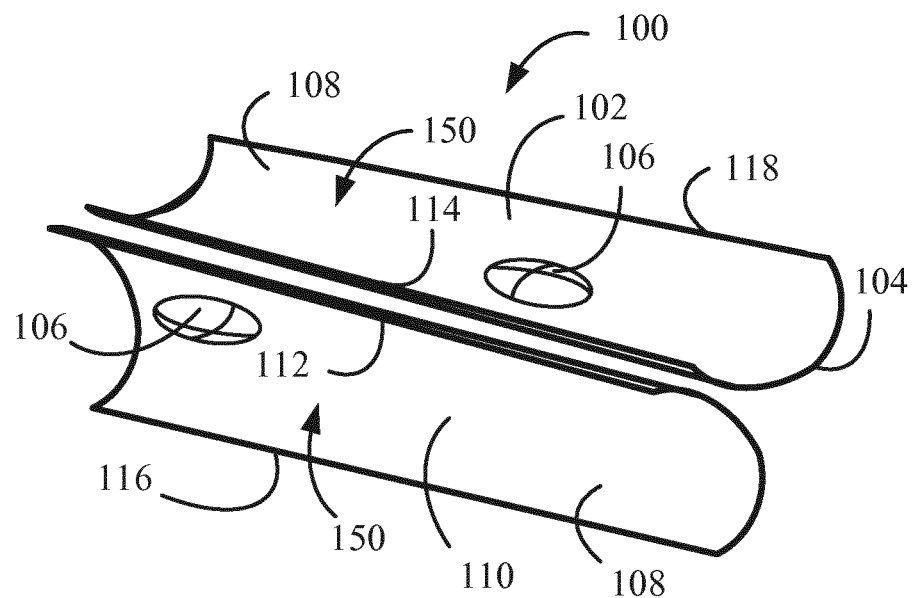
FIGS. 1A and 1B are elevated oblique and cross-section view simplified illustrations of an exemplary embodiment in accordance with the current method and apparatus.

The term "Anastomosis" as used in the present disclosure means the connection line at which a wall of a first vessel (e.g., vein, artery, synthetic graft) is attached to a wall of a second vessel (e.g., vein, artery or synthetic graft) allowing flow from a lumen of the first vessel into a lumen of the attached second vessel or vice versa. Such a connection may be performed with suturing or by other means.

The term "Fistula" as used in the present disclosure means an abnormal connection or passageway between an artery and a vein, and more particularly to such vascular passageways surgically created for hemodialysis treatments. In advanced stages, usually the vein substantially dilates and elongates in response to a much greater blood flow and shear stress, following the direct bypassing into the arterial system, and when it is large enough to allow cannulation, the fistula is defined as "mature."

The terms "Flow" and "Blood flow" are used interchangeably in the present disclosure and relate to flow of any type of fluid through a vessel.

The term "Plastically formable" as used in the present disclosure means the ability of an object's form to be changed from a first relaxed state to a second relaxed state.

The term "Elastically formable" as used in the present disclosure means the ability of an object's form to be stretched from a first relaxed state to a second non-relaxed state and to substantially resume its original shape once it non-stressed again.

The term "vessel" as used in the present disclosure is a biological vessel, namely an artery or a vein of biological vessel tissue. The vessel may be a so called autograft, which is a tissue graft obtained from one part of a patient's body for use on another part. Hence, the term "vessel" as used in the present disclosure is a vessel other than an artificial vessel or graft, which are e.g. made of biologically compatible synthetic materials like PTFE etc.

The term "rounding" as used in the present disclosure is in particular a junction rounding avoiding sharp edges or corners of a junction. The rounding is in particular provided for artifactual junctions of vessels, such as end-to-side anastomosis. Optionally, the rounding is in particular provided for a substantially sharp junction edge of an acute angle formed between adjoining vessels. The rounding is curved, such as partly circularly curved, i.e. not-straight. The rounding may accomplish resurfacing of a junction edge in order to diminish stagnant and/or turbulence areas proximal, within and/or distal the junction, by, for example, creating a hemodynamic shape. The rounding may be provided as an inward curve, i.e. a concave or concavish curvature having a central axis of the vessel closer to the curvature's center than to the curvature's ends. Examples of such a curve are a depression or an impression. Alternatively, the rounding may be provided as an outward curve, i.e. a convex or convexish curvature having a central axis of the vessel further away from the curvature's center than the curvature's ends. Examples of this kind of curve are a bulge, a bump or a protuberance. A curve may be formed following a compressive act or process, as in the case of creating a dent, in which a junction edge is inwardly pressed while decreasing a cross section of the junction neck. Alternatively, a curve may be formed following an expansive act or process, in which a junction edge is outwardly extended while increasing a cross section of the junction neck. Furthermore, the rounding may have a radius of a roundish curvature. The rounding may also be a fillet, i.e. a concave easing of the corner or a chamfer, i.e. having a beveled edge. Moreover, in one embodiment, the rounding is a rounding comprising two different portions, each portion having a rounding with a certain radius. Such a rounding can be seen in FIG. 12A or FIG. 12B. The rounding may also be provided as an arch or have an arch-like structure. A Rounding is not to be confused with contouring of a whole vessel, or a segment thereof, to have a certain curvature along its length. A Rounding in the present context should neither be confused with a shape of a cross section of the walls of a vessel.

The term "immediate vicinity" of an anastomosis includes a distance range of about 1-2 cm from the junction of the anastomosis.

DETAILED DESCRIPTION

An initiating event in the pathogenesis of venous stenosis in AV dialysis vascular access point grafts and fistulae is hemodynamic stress, especially in regions of low shear stress and turbulence at the graft-vein anastomoses. Another important initiating event is the high wall tension to which the vein graft is exposed. Under normal physiological conditions, the pressure in the venous circulation is 3-5 mmHg. After fistula creation, the mean pressure in the vein is 100 mmHg. Unlike arteries, veins have a relatively thin wall with thin muscularis layer. As a compensation reaction, while trying to adapt to the "new" physiological conditions and high pressures, the vein wall thickens in an attempt to reduce the sudden high wall tension. The pathological process of wall thickening is considered the seed of intimal hyperplasia and vein stenosis.

In neointimal hyperplasia the degree of luminal stenosis depends on both the magnitude of neointimal hyperplasia and degree of vascular remodeling. With the same amount of neointimal hyperplasia, vascular constriction and unfavorable remodeling results in luminal stenosis.

In end-to-side anastomosis an end of a vessel, usually a vein, is surgically affixed to a surgically created side opening in an artery. In this manner, a blood flow is obtainable from the artery into the vein through the side opening. The juncture at the side opening usually comprises vessel tissue edges and corners created by the surgical incisions or cuts and subsequent junction anastomosis.

Creating a rounding of these edged or cornered junctions can remove at least partly the edges and corners and replace them by an advantageous rounding of at least portions of the vessel wall(s) at the junction. As an alternative, the rounding may add volume to the edges and corners. This will be more elucidated in connection with the examples and drawings described hereinafter.

As mentioned above, the inventors of the present disclosure have realized that modification of the flow regime within a vessel may diminish or even eliminate areas of flow stagnation or turbulence and prevent the ill-effects such occurrences may have on the vessel.

Such modification may be applied externally to the vessel at hand, as will be explained in detail below, by applying pressure at predetermined locations along the vessel wall at which flow stagnation or turbulence are expected or found to exist and create one or more protrusion into the lumen of the vessel. Such protrusions, located appropriately and having an appropriate three-dimensional geometrical shape, when left in situ over a period of time may diminish or even eliminate areas of flow stagnation or turbulence and prevent the ill-effects such occurrences may have on the vessel. Such diminishing and/or elimination may be achieved immediately at protrusions formation, or be achieved after a prolonged process of tissue remodeling and hyperplasia by which the vessel expands towards the protrusions.

Figure 1B:
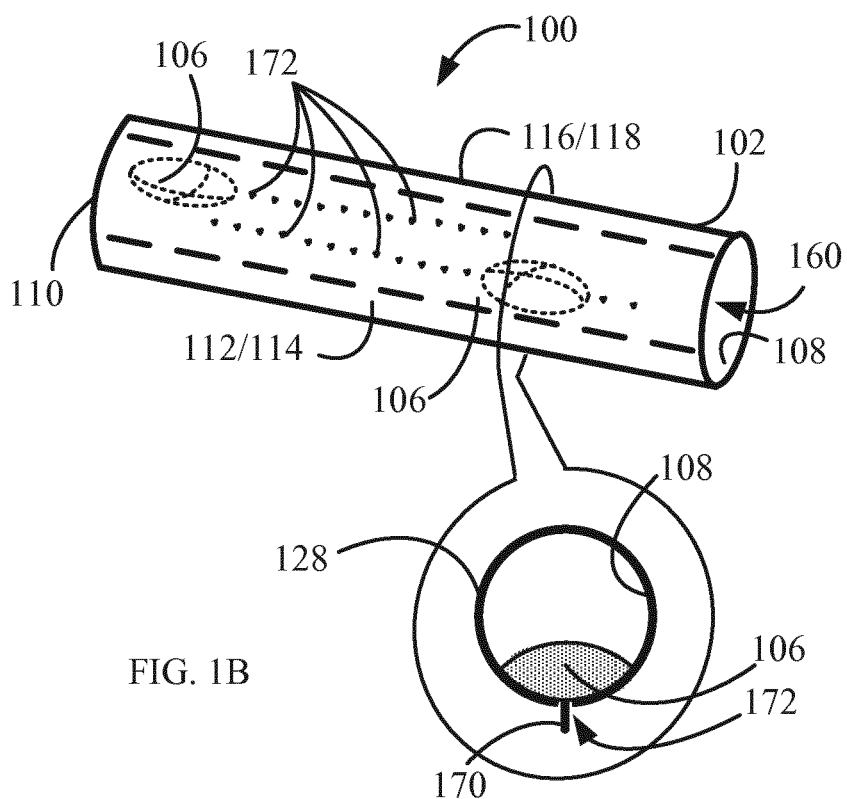

Reference is now made to FIGS. 1A and 1B, which are elevated oblique and cross-section view simplified illustrations of an exemplary embodiment in accordance with the current method and apparatus.

FIG. 1A illustrates a flow modifying external vascular support 100 in an open position including one or more vessel accommodating portions 102 and one or more cover portions 110, which may be separate from or at least partially attached to portion 102. Portion 102 may include an internal wall 108 having at least one concave surface 104 defining a trough 150. An internal wall 108 of portion 110 may also include at least one concave surface 104 defining a trough 150. Alternatively, either one of portions 102 and 110 may be a single member capable of rolling to a closed tubular shape.

FIG. 1B illustrates vascular support 100 in a closed position. In this configuration, for example purposes only, margin 112 of cover portion 110 may be attached to margin 114 of vessel accommodating portion 102 and margin 116 of cover portion 110 may be attached to margin 118 of portion 102. When closed, portions 102 and 110 define between them, or by each of portion 102 and 110 individually, one or more lumens 160 operative to accommodate and enclose one or more vessels. Vessel accommodating portion 102 and cover portion 110 may also include one or more flow modifying elements 106 protruding into lumen 160 from an internal wall 108 thereof, as will be described in greater detail below.

Vascular support 100 may be made of a plastically formable polymeric or metallic material such as, for example, a biocompatible stainless steel alloy (e.g., Cobalt-Chrome or Nickel-Titanium) and may be employed to shape portions of a vessel accommodated in lumen 160 as desired. Alternatively, vascular support 100 may be made of a rigid or semi-rigid material and have a mold-like form. In this configuration, vascular support 100 may be employed to shape a vessel accommodated in lumen 160 in a predetermined form and may also include plastically formable segments as will be described in greater detail below. Alternatively and optionally, vascular support 100 may be made of an elastic or non-elastic textile fiber or yarn.

Vascular support 100 walls may be porous or made of a mesh so that to allow tissue growth into and through the pores over time and/or prevent local ischemiaor damage to the vessel and enable adventitia growth.

Vascular support 100 may be restrictive, i.e., allowing vessel expansion up to a limit at which vessel walls are forced to acquire the shape of the internal walls of support 100; constrictive, i.e., narrowing segments of a vessel to force the vessel to acquire a predetermined shape; loosely overlaying or elastically radially expandable to a predetermined limit in relation to a vessel accommodated within the lumen of support 100.

Alternatively, vascular support 100 portions 102 and 110, separately or attached, may be bendable about said vessel to conform said vessel shape.

Flow modifying elements 106 may be made of a rigid material and be attached to internal wall 108 protruding into lumen 160. Elements 106 may be adhered to a location on internal wall 108 in real time, the location determined from a lookup chart or based on data received in real time as will be described in greater detail below.

Alternatively and optionally, elements 106 may be manufactured as an integral part of internal wall 108 or pre-attached and positioned at various predetermined locations on internal wall 108 so that to enable selection of the most appropriate vascular support 100 in real time.

In another embodiment, in accordance with the current method and apparatus, flow modifying elements 106 may be supplied at a variety of predetermined geometrical shapes and sizes, may include one or more pins 170 on one or more surfaces of element 106 and may be attached to support 100 internal wall 108 by insertion of pins 120 into one or more predetermined holes 172 in wall 128 of support 100.

In FIGS. 2A and 2B, which are elevated oblique and cross-sectional view simplified illustrations of yet another exemplary embodiment in accordance with the current method and apparatus, support 200 may include one or more plastically formable segments 220 at pre-determined locations. Flow modifying elements 206 may be formed in real time by, for example, applying pressure to external wall 222 of support 200 at plastically formable segments 220 and forming one or more invaginations 224 protruding into lumen 260 from internal wall 208. Segments 220 may have an area large enough to enable slight variations in invaginations 224 size and location within segment 220.

The parameters characterizing invaginations 224 (i.e., dimensions, location and similar) may be determined empirically in real time by employing, for example, templates including flow modifying elements of various sizes and locations in a method as will be described below, or selected from a lookup chart based on parameters characteristic of the selected vessel and location of support 200 placement on the vessel.

Figure 2C:
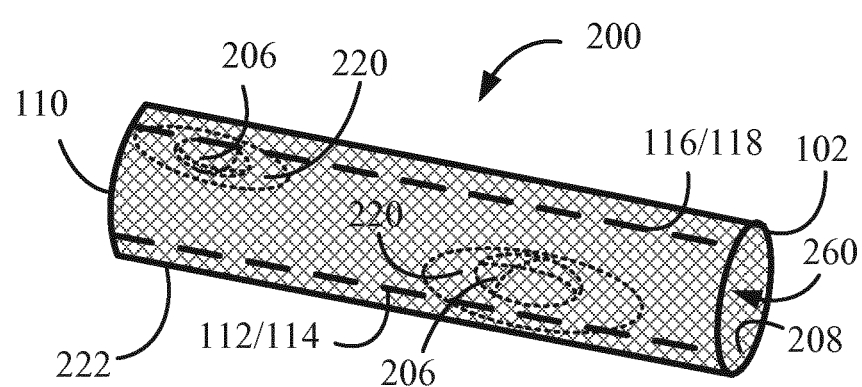

As shown in FIG. 2C, which is an elevated oblique view simplified illustration of yet another exemplary embodiment in accordance with the current method and apparatus, support 200, as a whole, may be plastically formable and may be shaped and molded in real time as desired. In this embodiment, flow modifying elements 206 may be formed at any desired location in the same fashion explained above and may have any desirable dimensions. Alternatively, support 200, as a whole, may be elastically formable and include flow modifying elements 206 pre-attached or attached in real time.

Alternatively and optionally, support 200 may be radially plastically formable towards the central axis of lumen 260 only.

Alternatively and optionally, support 200 may be made of a material that may harden over time, as a result of a change in temperature or by other means and be made to retain its newly formed shape. Alternatively, support 200 including flow modifying elements 206 may be provided in a pre-defined shape and having a rigid non-formable state.

Figure 3:
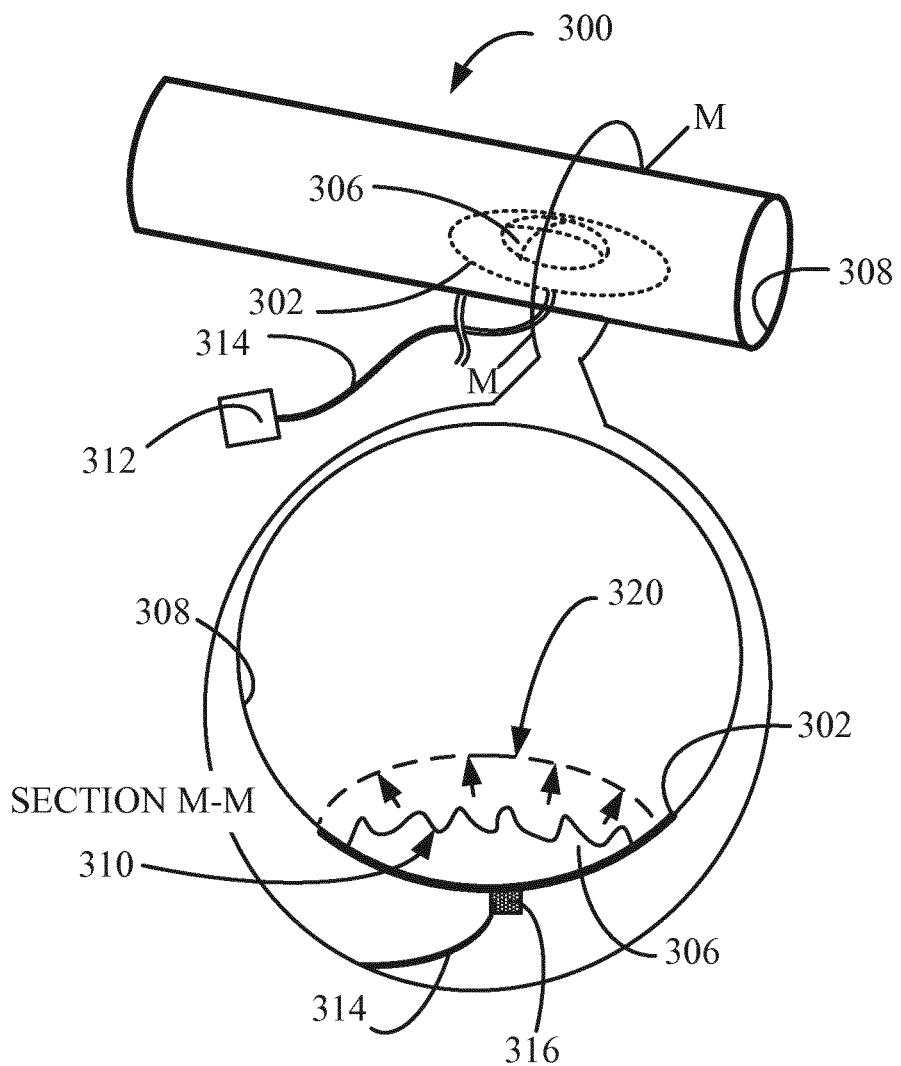
FIG. 3 is an elevated oblique and cross-section view simplified illustration of another exemplary embodiment in accordance with the current method and apparatus.

Reference is now made to FIG. 3, which is an elevated oblique and cross-section view simplified illustration of still another exemplary embodiment in accordance with the current method and apparatus. Flow modifying element 306 may be affixed to a base 302. Base 302 may be attached by adhesion, radial constriction or any other method to internal wall 308 of vascular support 300. Flow modifying element 306 may be loosely sustained as shown in FIG. 3 or be in a partially pre-stretched form and may be expandable in a direction indicated by arrows from an initial state 310, to an expanded state 320 indicated by a phantom line.

Element 306 may be supplied by a source 312 such as a syringe or pump via one or more supply tubing 314 connected to one or more one-way or two-way valves 316 on element 306 or Base 302. Element 306 may be expanded by employing a biocompatible fluid such as saline or a biocompatible material having an initial fluid state that may become plastic in nature or harden over time as a result of a change in temperature or by other means and be made to retain its newly formed shape.

Source 312 and supply tubing 314 may be detached once element 306 has been expanded to a desired dimension. The parameters characterizing expandable element 306 (i.e., dimensions, location and similar) in its expanded form may be determined empirically in real time by employing, for example, templates including flow modifying elements of various sizes and locations or selected from a lookup chart based on parameters characteristic of the selected vessel and location of the procedure on the vessel.

Figure 4A:
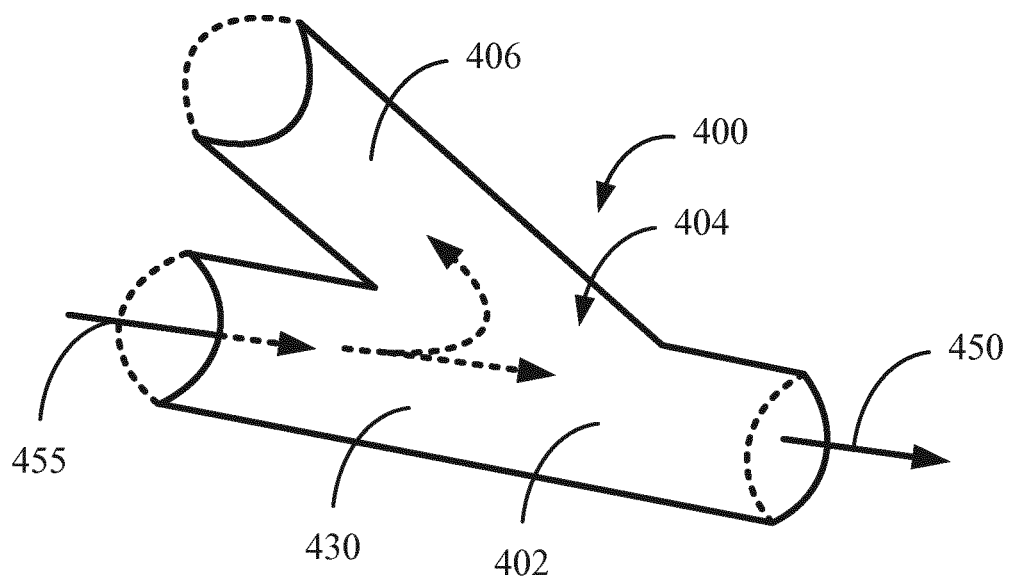
FIGS. 4A and 4B are sectional view simplified illustrations of blood flow through a typical AV anastomosis.
Figure 4B:
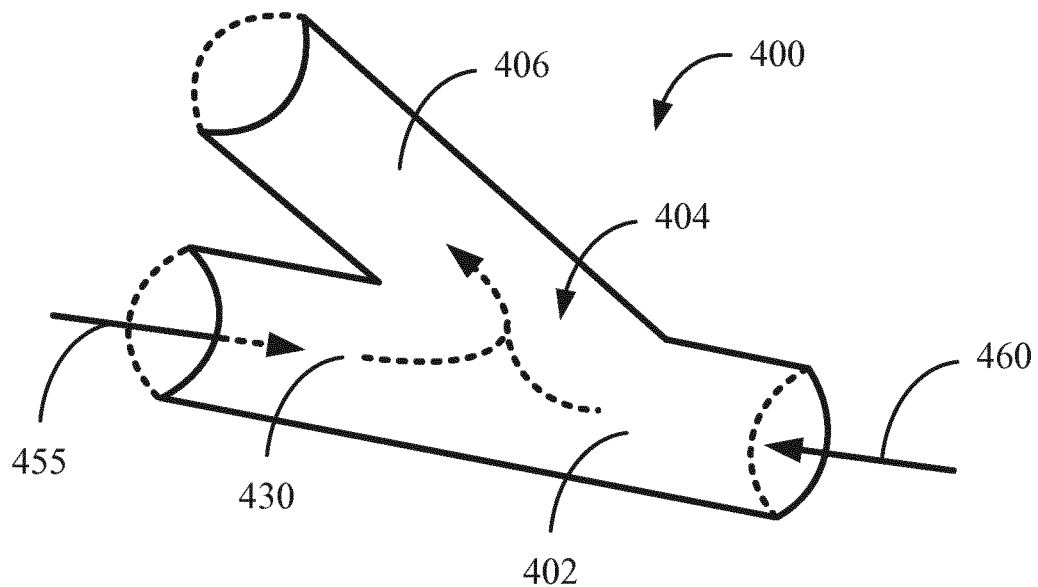

Referring now to FIGS. 4A and 4B, which are sectional view simplified illustrations in which part of the vessel walls has been removed for purposes of explanation. FIGS. 4A and 4B, demonstrate blood flow through a typical AV anastomosis 400 as commonly employed in preparation of vascular access for a dialysis procedure. The section is taken along a plane parallel to the central axes of the anastomosed vessels. The fluid dynamics of the flow of blood through the anastomosis depends, among others, on the artery selected for the vascular access anastomosis procedure and the location along that artery at which the procedure is performed.

In FIG. 4A blood flow exits (arrow 450) arterial portion 402 of anastomosis 400 in the same direction in which it has entered (arrow 455). A portion of the blood flowing through arterial portion 402 of host artery 430 branches through an arteriovenous (AV) fistula 404 into an graft/vein 406 portion of anastomosis 400. Such a situation exists, for example, when the vascular access anastomosis procedure is performed above the elbow, for example, between the Brachial artery and the Basilic or the Cephalic veins.

In FIG. 4B blood flow enters anastomosis 400 from both ends of arterial portion 402, in opposite directions of flow, as indicated by arrows 455 and 460. A portion of the blood flowing through arterial portion 402 of host artery 430 may branch through arteriovenous (AV) fistula 404 into a graft/vein 406 portion of anastomosis 400. Such a situation exists, for example, when the vascular access anastomosis procedure is performed below the elbow, for example, between the Radial artery and the Median Antebrachial or Cephalic veins.

The inventors of the current method and apparatus have employed Computerized Fluid Dynamics (CFD) analysis using CFX software by ANSYS, Inc. (ANSYS, Inc., headquartered in Canonsburg, Pa., United States) together with relevant clinical flow data from the literature to carry out blood flow simulations as a tool for analyzing the fluid dynamics of blood flow through anastomosed vessels such as those depicted in FIGS. 4A and 4B. The simulations, which relies on known physiological and anatomical data and assumptions from various clinical and pre clinical studies provide information that may lead to anastomosis configuration and vessel wall modification optimizing the blood flow dynamics through such anastomoses, minimizing and maybe preventing hemodialysis vascular access dysfunction. Partial results of the aforementioned simulations are shown in FIGS. 5A, 5B, 6A and 6B.

Figure 5A:
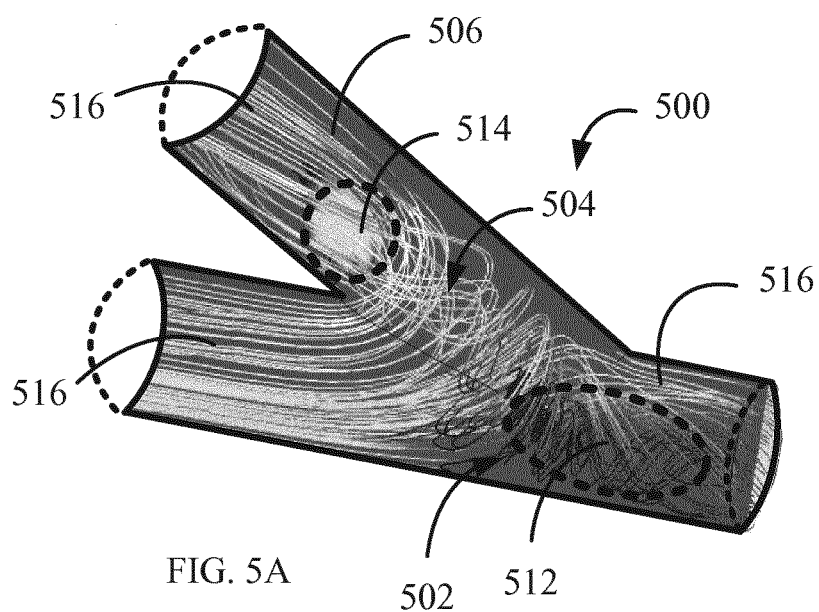
FIG. 5A is a sectional view computerized Fluid Dynamics (CFD) simulation rendering.
Figure 5B:
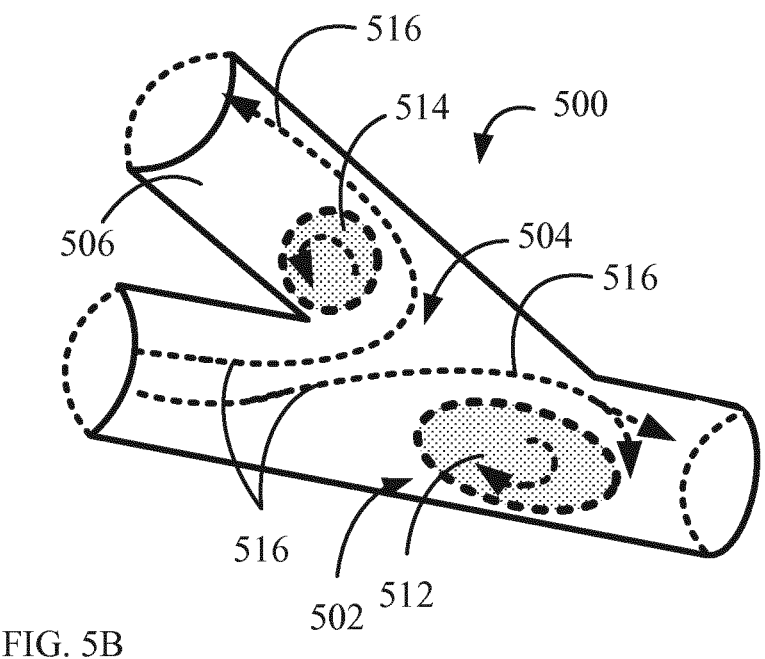
FIG. 5B is a sectional view simplified illustration of FIG. 5A.

Reference is now made to FIG. 5A, which is a sectional view computerized CFD simulation rendering and FIG. 5B, which is a sectional view simplified illustration of FIG. 5A, depicting flow of blood through anastomosed vessels such as those of FIG. 4A. In FIGS. 5A and 5B part of the vessel walls has been removed for purposes of explanation to demonstrate one or more (in this case—two) zones which appear to be characterized by low velocity. A first zone 512 in the arterial area 502, the "heel", opposite AV fistula 504 and a second zone 514 in propinquity to AV fistula 504 or in vein/AV shunt graft 506 portion of anastomosed vessels 500. Either one of, or both zones 512 and 514 may be associated with low shear stress and turbulence and may, in time, produce intimal hyperplasia, thrombi or other complications leading to vascular access failure in the maturing stage of the vascular access. A partial, more uniform substantially laminar flow 516 is noted to bypass zones 512/514.

Figure 6A:
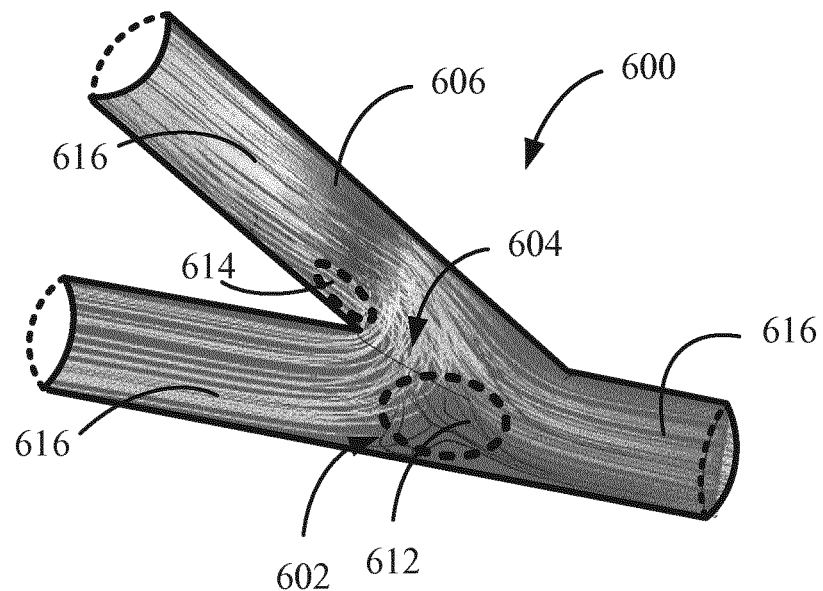
FIG. 6A is a sectional view computerized CFD simulation rendering.
Figure 6B:
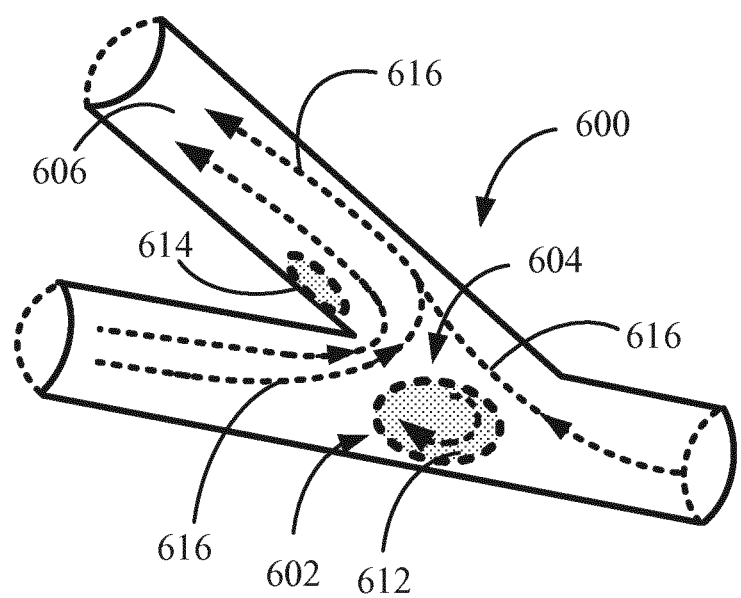
FIG. 6B is a sectional view simplified illustration of FIG. 6A.

FIG. 6A, which is a sectional view computerized CFD simulation rendering and FIG. 6B, which is a sectional view simplified illustration of FIG. 6A, depict flow of blood through an anastomosed vessels such as those of FIG. 4B. In FIGS. 6A and 6B part of the vessel walls has been removed for purposes of explanation to demonstrates one or more (in this case—two) zones which appear to be characterized by low velocity, similar to the zones 512/514 described in FIGS. 5A and 5B. A first zone 612 in the arterial area 602, the "heel", opposite fistula 604 and a second, smaller zone 614 in AV fistula 604 or vein/AV shunt graft 606 portion of anastomosed vessels 600. Either one of or both zones 612 and 614 may be associated with low shear stress and turbulence and may, in time, produce intimal hyperplasia, thrombi or other complications leading to failure in the maturing stage of the vascular access. A partial, more uniform substantially laminar flow 616 is noted to bypass zones 612/614.

As experimentation shows and is illustrated in FIGS. 5A, 5B, 6A and 6B, each zone is characterized by parameters such as geometrical form, vessel type and diameter of vessel walls, distance from vessel wall, flow patterns and rates and computerized fluid dynamics print. The locations of zones 512/514 612/614 along the vessel are variable and depend on the vessels selected for the vascular access anastomosis procedure, the selected anatomical location of the procedure (e.g. the diameter of the artery and vein cross-section) and the physiological conditions on the anastomosis site (e.g. flow rates, blood pressure, extensiveness of the atherosclerosis in the artery).

It should also be noted that stagnant and/or turbulent areas, such as zones 512/514 612/614, may occur in various numbers and/or at various locations in propinquity to the intersection of the vessels.

Figure 7A:
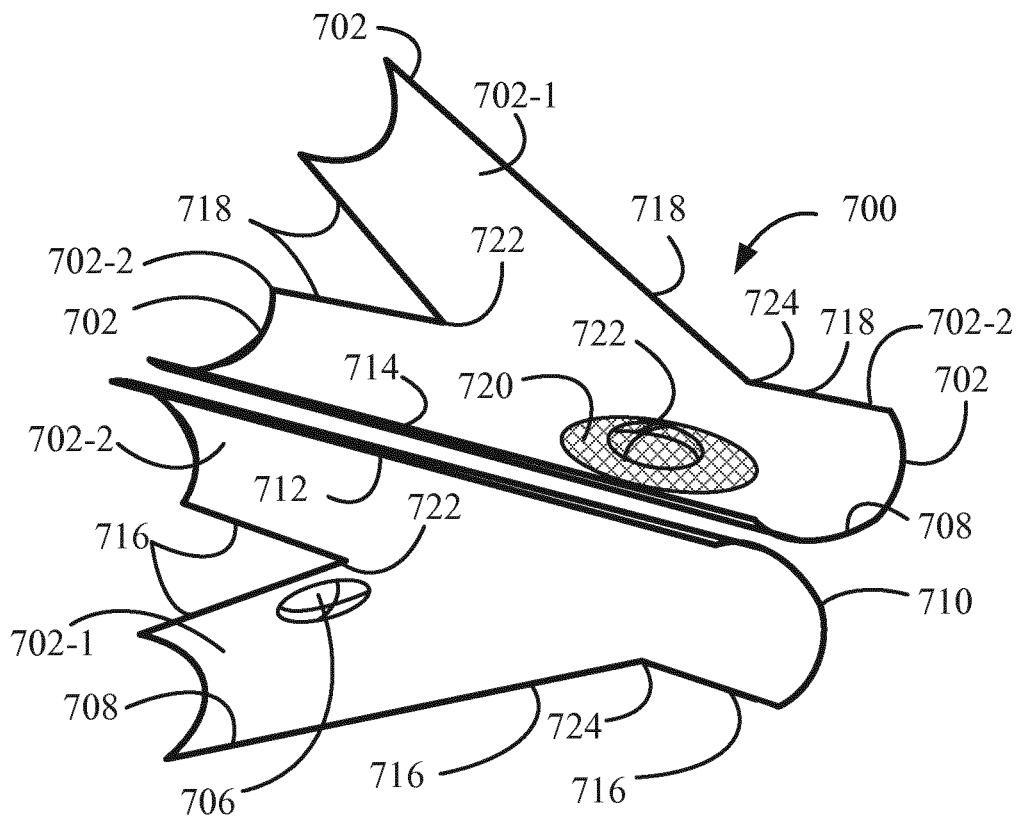
FIGS. 7A and 7B are elevated oblique view simplified illustrations of another exemplary embodiment in accordance with the current method and vascular apparatus.
Figure 7B:
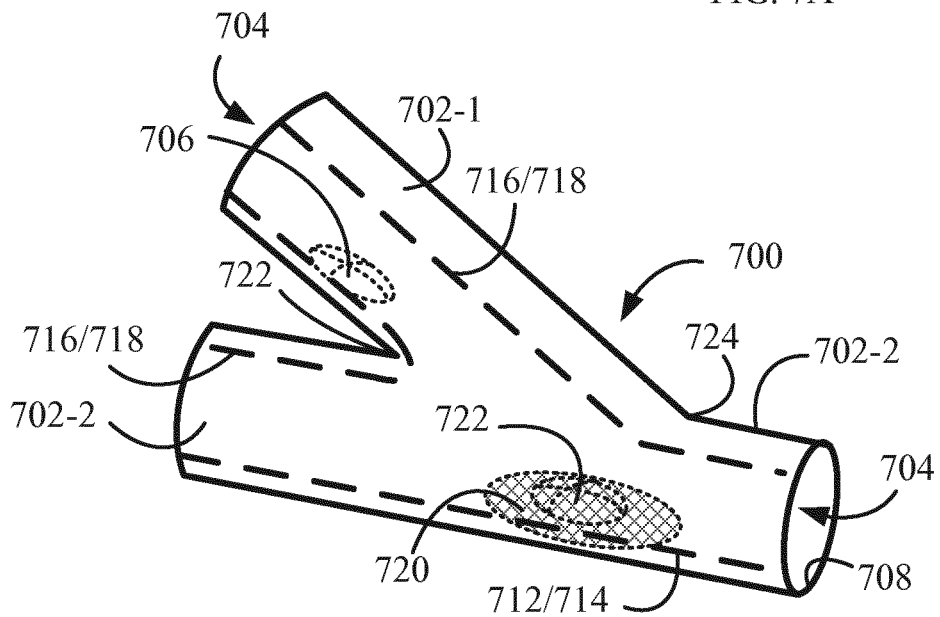

Reference is now made to FIGS. 7A and 7B, which are elevated oblique view simplified illustrations of another exemplary embodiment in accordance with the current method and apparatus. FIGS. 7A and 7B illustrate a flow modifying vascular support 700 designed for an AV anastomosis as commonly employed in preparation of vascular access for a dialysis procedure as described above.

FIG. 7A depicts vascular support 700 in an open position including one or more vessel accommodating portion 702 having one or more branches 702-1 and 702-2 intersecting at an angle less that 90 degrees and one or more cover portions 710 having one or more branches 702-1 and 702-2 intersecting at an angle less that 90 degrees. Vessel accommodating portions 702-1 and 702-2 define between them acute angle 722 and obtuse angle 724 opposite to acute angle 722.

When closed, portions 702 and 710 define between them one or more lumens 704 operative to accommodate and enclose one or more vessels. Alternatively, portions 702 and 710 may be at least partially connected, each at least partially enclosing one or more vessels individually.

Cover portion 710 may be separate from, or at least partially attached to vessel accommodating portion 702. Vessel accommodating portion 702 and/or cover portion 710 may also include one or more flow modifying elements 706 attached to an internal wall 708 of either one or both portions 702 and 710.

FIG. 7B illustrates vascular support 700 in a closed position. In this configuration, for example purposes only, margin 712 of cover portion 710 may mirror and be attached to margin 714 of vessel accommodating portion 702 and margin 716 of cover portion 710 may be attached to margin 718 of vessel accommodating portion.

When closed, vessel accommodating portion 702 and cover portion 710 define between them one or more lumens 704 intersecting at an angle less than 90 degrees, operative to accommodate and at least partially enclose one or more vessels. One or more lumens 704 may include one or more flow modifying elements 706 protruding into lumen 704 from an internal wall 708 thereof.

Vascular support 700 may be made of a plastically formable polymeric or metallic material such as, for example, a biocompatible stainless steel alloy (e.g., Cobalt-Chrome or Nickel-Titanium) and may be employed to shape a vessel accommodated in lumens 704 as desired. Alternatively, vascular support 700 may be made of a rigid or semi-rigid material and have a mold-like form. In this configuration, vascular support 700 may be employed to shape anastomosed vessels accommodated in lumens 704 in a predetermined form and may also include plastically formable segments. Alternatively and optionally, vascular support 700 may be made of an elastic or non-elastic textile fiber or yarn.

Vascular support 700 walls may be porous or made of a mesh so that to allow tissue growth into and through the pores over time.

Vascular support 700 may be restrictive, i.e., allowing vessel expansion up to a limit at which vessel walls are forced to acquire the shape of the internal walls of support 700, constrictive, i.e., narrowing segments of a vessel to force the vessel to acquire a predetermined shape, loosely overlaying or elastically radially expandable to a predetermined limit in relation to anastomosed vessels accommodated within the lumen of support 700.

Alternatively, vascular support 700 portions 702-1 and 110, separately or attached, may be bendable about said vessel to conform said vessel shape.

Alternatively and optionally, vascular support 700 may be made of a rigid material and have a mold-like form operative to shape anastomosed vessels accommodated in lumen 704 in a pre-determined three-dimensional geometric shape. Additionally and optionally, vascular support 700 may also include plastically formable portions 720 similar to portions 220 shown in FIGS. 2A and 2B to be formed into flow modifying elements 722.

Vascular support 700 walls may be porous or made of a mesh so that to allow tissue growth into and through the walls over time.

Alternatively and optionally, vascular support 700 may be made of an elastic or non-elastic textile fiber or yarn.

Flow modifying elements 706 may be made of a rigid material and be adhesively attached to or be manufactured as an integral part of internal wall 708 protruding into lumen 704. Elements 706 may be adhered to a location on internal wall 708 in real time, the location determined empirically or selected from a lookup chart or, alternatively and optionally, manufactured pre-attached at various predetermined locations on internal wall 708, so that to enable selection of the most appropriate vascular support 700 in real time.

Selection of the location and dimensions of flow modifying elements 706 may be based on results of simulations as shown in FIGS. 5A, 5B, 6A and 6B and additional or other factors such as parameters (e.g. such as diameter of vessel wall, vessel type, etc.) characteristic of the selected vessel and location of the vascular access anastomosis procedure on the vessel. These considerations are aimed at minimizing or even eliminating zones such as 512/514 (FIG. 5) and 612/614 (FIG. 6) that may be associated with low shear stress and turbulence as described above.

Additionally or alternatively, the selection of the location and dimensions of flow modifying elements 706 may also be based on real time parameters collected during the vascular access anastomosis procedure.

Figure 8A:
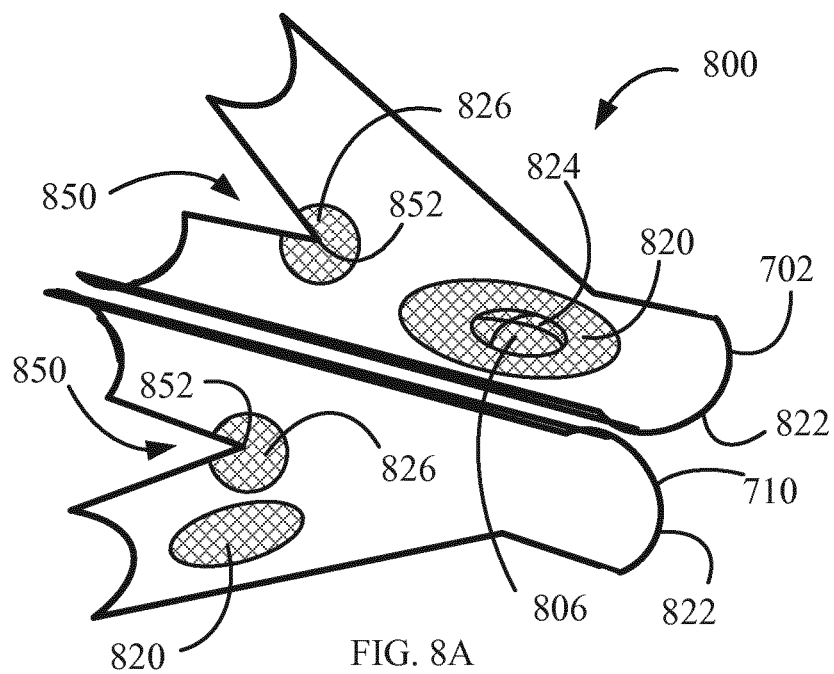
FIGS. 8A and 8B are elevated oblique view simplified illustrations of yet another exemplary embodiment in accordance with the current method and vascular apparatus.
Figure 8B:
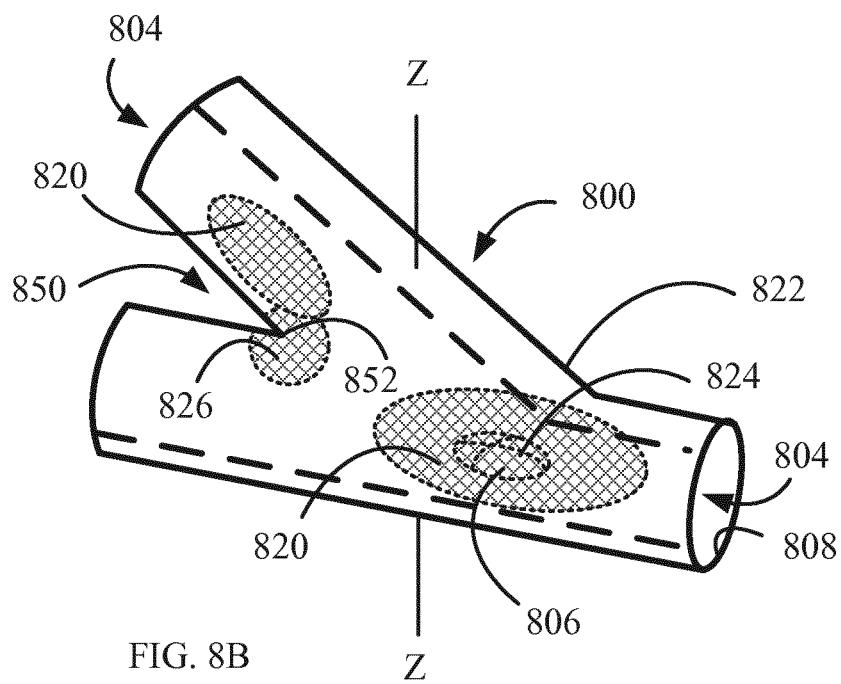

Reference is now made to FIGS. 8A and 8B, which are elevated oblique view simplified illustrations of yet another exemplary embodiment in accordance with the current method and vascular support. Support 800 may include one or more formable portions 820 at pre-determined locations.

Flow modifying elements 806 may be formed in real time by, for example, applying pressure to modify external wall 822 of support 800 at plastically formable portions 820 and forming one or more invaginations 824 protruding into lumen 804 from internal wall 808. The parameters characterizing invaginations 824 (i.e., dimensions, location and similar) may be determined empirically in real time by employing, for example, templates including flow modifying elements of various sizes and locations or selected from a lookup chart based on parameters characteristic of the selected vessel and location of the procedure on the vessel.

Additionally and optionally, support 800 may also include a plastically formable portion 826 at acute angle 850 to enable molding pointed junction 852 of the vessels being anastomosed (not shown) into a rounded junction as will be explained in greater detail below.

Figure 9A:
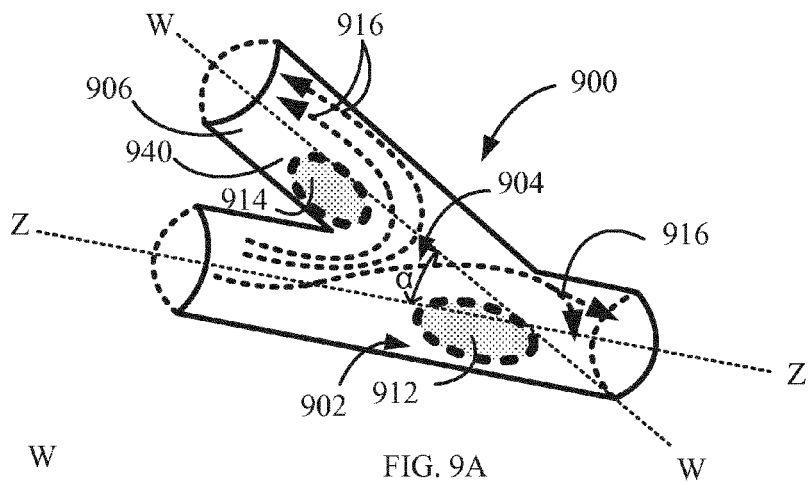
FIGS. 9A, 9B and 9C are sectional view simplified illustrations depicting an effect of a change in an angle ($\alpha$) on flow through an anastomosis.
Figure 9B:
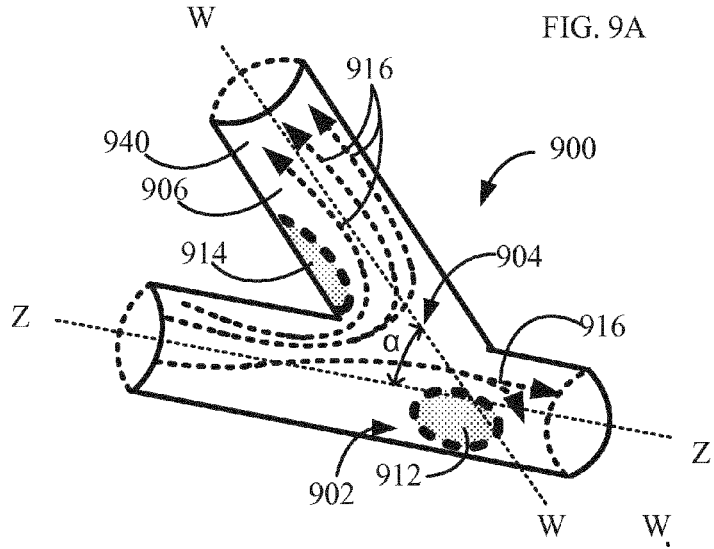
Figure 9C:
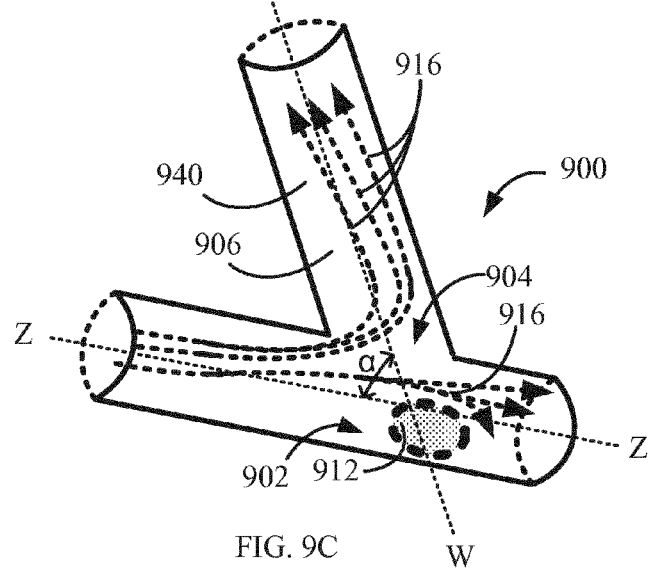

FIGS. 9A, 9B and 9C, which are sectional view simplified illustrations depicting an effect of a change in an angle ($\alpha$) on blood flow through an anastomosis. In FIGS. 9A, 9B and 9C part of the vessel walls has been removed for purposes of explanation. Angle ($\alpha$) is defined as the angle at a point of intersection between central axis (Z) of artery 930 and central axis (W) of vein 940. Changes in the aforementioned parameters characterizing each of zones 512/514 and 612/614 are followed in view of corresponding changes in angle ($\alpha$).

In FIG. 9A, angle ($\alpha$) may be approximately 30 degrees ($\alpha=30°$). Two zones 912 and 914 similar to aforementioned zones 512/514 and 612/614 are noticed. Zone 912 in the arterial area 902, the "heel", opposite AV fistula 904 and a second zone 914 in propinquity to AV fistula 904 or in vein/AV shunt graft 906 portion of anastomosed vessels 900. A partial, more uniform substantially laminar flow 916 is noted to bypass zones 912/914.

In FIG. 9B, angle ($\alpha$) may be approximately 45 degrees ($\alpha=45°$). At this angle, zones 912/914 appear to be smaller than zones 912/914 of FIG. 9A and may have taken on a different geometrical form. These changes appear to have effected a uniform substantially laminar flow 916 of a larger volume of blood flowing through vein/AV shunt graft 906 portion of anastomosed vessels 900 than the volume of substantially laminar flow through the same region at ($\alpha=30°$) as depicted in FIG. 9A.

In FIG. 9C, angle ($\alpha$) may be approximately 60 degrees ($\alpha=60°$). At this angle, zone 914 appears to have been eliminated and the flow through AV fistula 904 or vein/AV shunt graft 906 portion of anastomosed vessels 900 appears to be substantially laminar. Zone 912 also appears to be smaller than at ($\alpha=30°$) and ($\alpha=45°$) of corresponding FIGS. 9A and 9B. These changes, in general, appear to have effected a uniform substantially laminar flow 916 on a larger volume of blood flowing through anastomosed vessels 900 than the volume of substantially laminar flow depicted in FIGS. 9A and 9B.

As shown above, for each artery and vein pair selected for the vascular access anastomosis procedure as well as the selected anatomical location on the artery and the vein pair at which the procedure is to be performed and the physiological conditions at the anastomosis site (e.g. flow rates, blood pressure) an optimal angle ($\beta$) may be determined at which zones associated with low shear stress and turbulence such as zones 512/514, 612/614 and 912/914 may be reduced or even eliminated and laminar flow substantially increased contributing to the prevention of vascular access procedure failures. An optimal angle ($\beta$) may be obtained empirically by employing, for example, templates having various angles ($\alpha$) or taken from a lookup chart based on parameters characteristic of the selected vessel and location of the procedure on the vessel.

Experimentation has shown, for example purposes only, that under the specific experiment conditions set by the inventors, the optimal angle (β) for an AV anastomosis performed on the Brachial artery was found to be about 45 degrees (α=45°), the optimal angle (β) for an AV anastomosis performed on the Radial artery in a configuration such as that depicted in FIG. 1B was found to be greater than 60 degrees (α>60°) and the optimal angle (β) for an AV anastomosis performed on the Radial artery in a configuration such as that depicted in FIG. 1A was found to be about than 30 degrees (α=30°).

Figure 10:
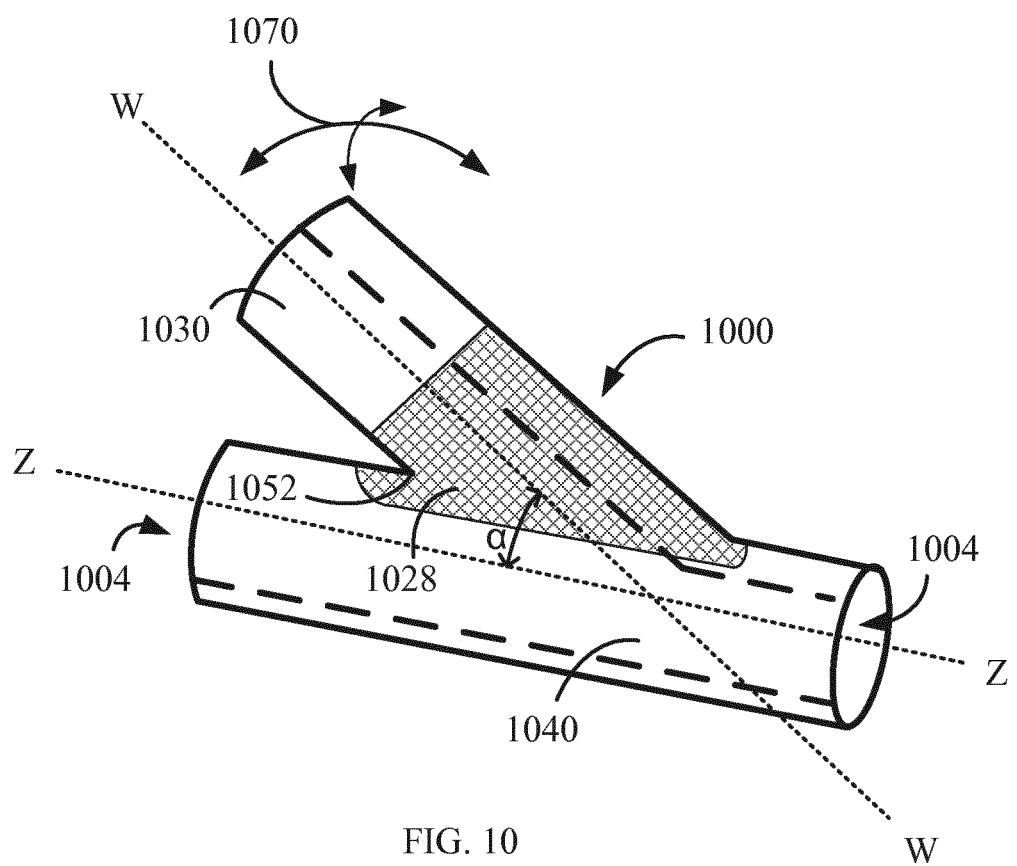
FIG. 10 is an elevated oblique view simplified illustration of still another exemplary embodiment in accordance with the current method and vascular apparatus.

Referring now to FIG. 10, which is an elevated oblique view simplified illustration of still another exemplary embodiment in accordance with the current method and apparatus. In FIG. 10, support 1000 may also include a plastically formable portion 1028 fully enveloping the junction of a support portion 1030 accommodating an vein/AV shunt graft (not shown) with support portion 1040 accommodating the host artery (not shown). This embodiment enables manipulation of portion 1030 relative to portion 1040 to vary angle (α) as explained above or to vary the special relationship between portions 1030 and 1040 by tilting or rotating portion 1030 relative to portion 1040 as indicated by arrows 1070 in order to optimize blood flow through the fistula (not shown). Alternatively, support 1000 may be pre-manufactured having a variety of various fixed predetermined angles (α).

Formable portion 1028 may also be employed to mold pointed junction 1052 of the vessels being anastomosed (not shown) into a rounded junction as will be explained in greater detail below.

Alternatively and optionally, support 1000, as a whole, may be plastically formable, similar to support 200 of FIG. 2C and may be shaped and molded in real time as desired. In this embodiment, flow modifying elements 706 (FIGS. 7A and 7B) may be formed at any desired location and may have any desirable dimensions.

Figure 11:
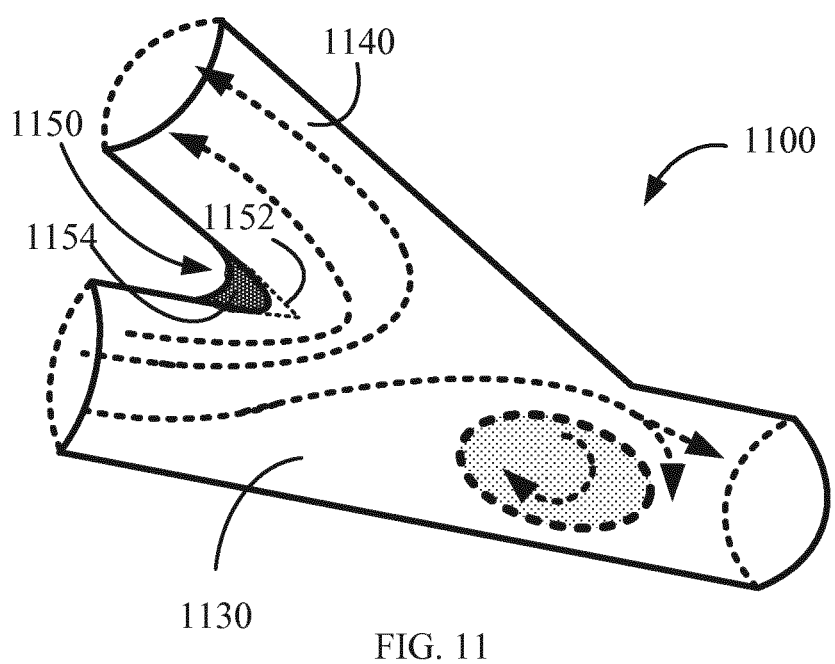
FIG. 11 is a sectional view simplified illustration depicting an effect of rounding an acute angle formed at the junction of walls of anastomosed vessels on flow through an anastomosis.

It was found that it may be difficult to completely eliminate zones associated with low shear stress and turbulence such as zones 512/514, 612/614 and 912/914 by variation of angle (α) alone. It was also found, as illustrated in FIG. 11, which is a sectional view simplified illustration in which part of the vessel walls has been removed for purposes of explanation to depict an effect of rounding an acute angle formed at the junction of walls of anastomosed vessels on blood flow through the anastomosis, that other factors such as, for example shaping acute angle 1150 from a pointed junction 1152 to a rounded junction 1154 at the point of joining of vein 1140 and artery 1130 substantially diminished zone 914 (FIG. 9). The radius of rounded junction 1154 may be obtained in real time by employing, for example, templates or selected from a lookup chart based on parameters characteristic of the selected vessels and location of the procedure on the vessels.

The rounded junction may has a curvature with a radius of curvature in the range of 0.25 mm to 4 mm, preferably in the range of 0.5 mm to 2.5 mm. A vascular support is provided with a rounding that has a curvature with a radius of curvature in the range of 0.25 mm to 4 mm, preferably in the range of 0.5 mm to 2.5 mm for providing said vessel junction with said junction rounding of corresponding shape and size when in apposition with the junction.

In summary, it appears that modifying flow in vessels employing, for example, flow modifying elements protruding into the lumen of a vessel, as will be demonstrated below, may substantially reduce or even eliminate zones associated with low shear stress and turbulence such as zones 512/514, 612/614 and 912/914, increase substantially laminar flow and contribute to the prevention of vascular access procedure failures. The results of experimentation and simulations as explained above may be analyzed and compiled into a lookup chart or any other reference that may be employed to predetermine the dimensions and locations of flow modifying elements of a vascular support as will be described in greater detail below.

Figure 12A:
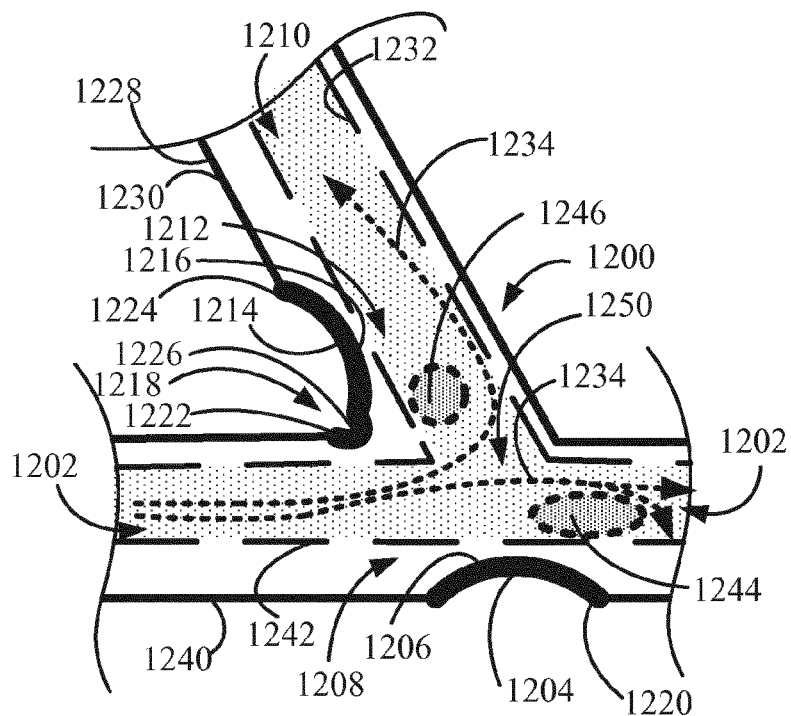
FIGS. 12A and 12B are cross-sectional view simplified illustrations depicting implementation of a flow modifying apparatus of FIGS. 8A-8B in accordance with the current method and vascular apparatus.
Figure 12B:
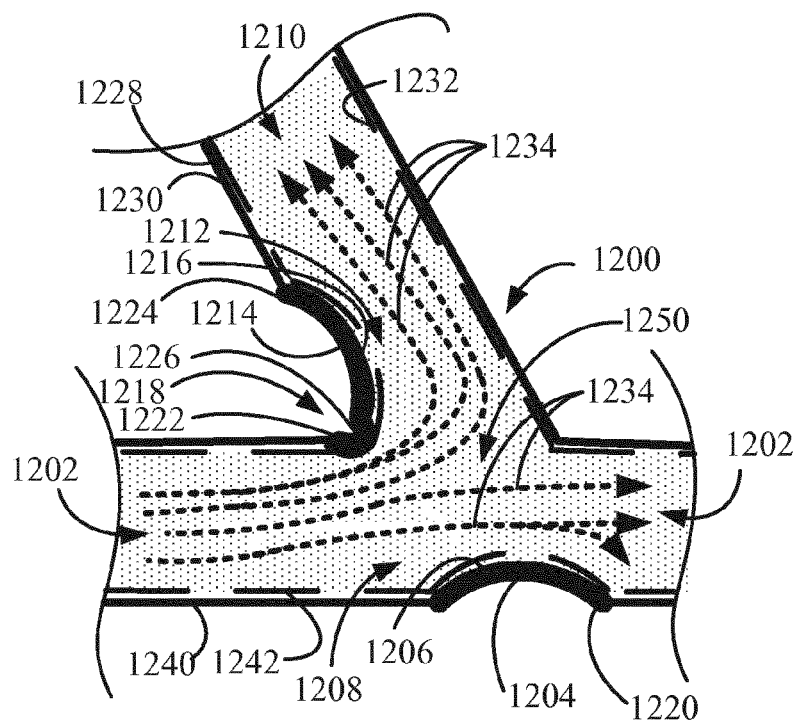

Referring now to FIGS. 12A and 12B, which are cross-sectional view simplified illustrations depicting implementation of a flow modifying support such as that shown in FIG. 8B, taken along axis Z-Z, in accordance with the current method and apparatus. Vascular support 1200 shown in FIGS. 12A and 12B is of the restrictive type, allowing the expansion of vessel walls 1232/1242 up to a predetermined limit.

Support 1200 may be made of a rigid, semi-rigid or elastically radially expandable to a predetermined limit in relation to a vessel accommodated within the lumens 1202 and 1210.

Support 1200 may also include one or more plastically formable, elastic or rigid, pre-shaped portions 1220, 1222 and 1224 the location and dimensions of which are predetermined and taken from a lookup chart based on parameters characteristic of the selected vessel and location of the procedure on the vessel.

Portion 1220 at the "heel" area 1208 opposite AV fistula 1250 has been pressed inward, into lumen 1202 of support 1200, forming an invagination 1204 creating a flow modifying element 1206.

Portion 1222 at acute angle 1218 has been pressed inward to mold and round junction 1226.

Portion 1224 at an area 1212 juxtaposing AV fistula 1250 has been pressed inward either in real time or, alternatively, has been pre-selected with portions 1224 and 1212 already pre-pressed (formed) inward, into lumen 1210 of support 1200 forming an invagination 1214, creating a flow modifying element 1216.

As shown in FIG. 12A, vascular support 1200 portion 1230 accommodates vein/AV shunt graft 1232 and vascular support 1200 portion 1240 accommodates host artery 1242. Support 1200 is larger in diameter that vein/AV shunt graft 1232 and host artery 1242 not affecting the flow regime inside the vessels at this stage.

FIG. 12A demonstrates one or more (in this case—two) zones which appear to be characterized by low velocity, a first zone 1244 in host artery 1242, the "heel", opposite fistula 1500 and a second zone 1246 in propinquity to AV fistula 1500 or in vein/AV shunt graft 1232.

Blood pressure within the vessels causes walls of host artery 1242 and vein/AV shunt graft 1232, represented in FIGS. 12A and 12B by a broken line, to press against and follow the contour of internal wall 1228 of support 1200.

Blood flowing through fistula 1250 supported by vascular support 1200 is affected by flow modifying elements 1206, 1216 and rounded junction 1226 and flows in a uniform substantially laminar flow 1234 as explained above. In this configuration, zones 1244 and 1246, similar to zones 512/514 (FIG. 5), 612/614 (FIG. 6) and 412/414 (FIG. 4), which may be associated with low shear stress and turbulence are either significantly diminished or completely eliminated.

In summary, application of vascular support 1200 may include identifying locations and dimensions of regions of low shear stress and turbulence 1244 and 1246 in anastomosed vessels flow regime, analyzing the parameters of regions 1244 and 1246, selecting a tridimensional flow modifying element 1206\1216 shape known to at least diminish regions 1206\1216 based on the analysis and modifying or selecting a template to modify one or more walls of the anastomosed vessels 1232 and 1242 at one or more locations corresponding to one or more regions 1206/1216, evaluating the effect of tridimensional flow modifying element 1206\1216 on the flow regime and replacing the template with a selected pre-manufactured support 1200 or externally adjusting the support 1200 modification as necessary to diminish or eliminate one or more of regions 1206/1216.

According to Roy-Chaudhury et al., "Early Arteriovenous Fistula Failure: A Logical Proposal for When and How to Intervene" (in Clinical Journal of the American Society of Nephrology 1:332-339, 2006) blood vessels try to maintain their original level of shear stress. An increase in flow and consequently shear stress (flow being directly proportional to shear stress) invariably results in vascular dilation as an attempt to reduce the shear stress applied to the vessel wall.

To accommodate for the post-procedure expansion in vessel wall diameter, any one of the supports brought forth in FIGS. 7A, 7B, 8A, 8B and 10 selected for a vascular access procedure in accordance with the considerations explained above, may also be selected to have a diameter larger in size than the pre-procedure diameter of a vessel to be accommodated in and supported by the selected support. This will allow for the post-procedure expansion of the vessel accommodated in the support as described by Roy-Chaudhury et al., eventually pressing against and following the contour of the internal wall of the selected support as described above.

Further experimentation and simulations carried out by the inventors of the current method and apparatus have confirmed the findings of Roy-Chaudhury et al. in that post procedure radial expansion, especially of the venous portion, may occur and form a significant contributing factor to the development of neointimal hyperplasia. Also, it was found that applying external support to the venous portion of the AV anastomosis may prevent the development of hyperplasia.

Figure 13A:
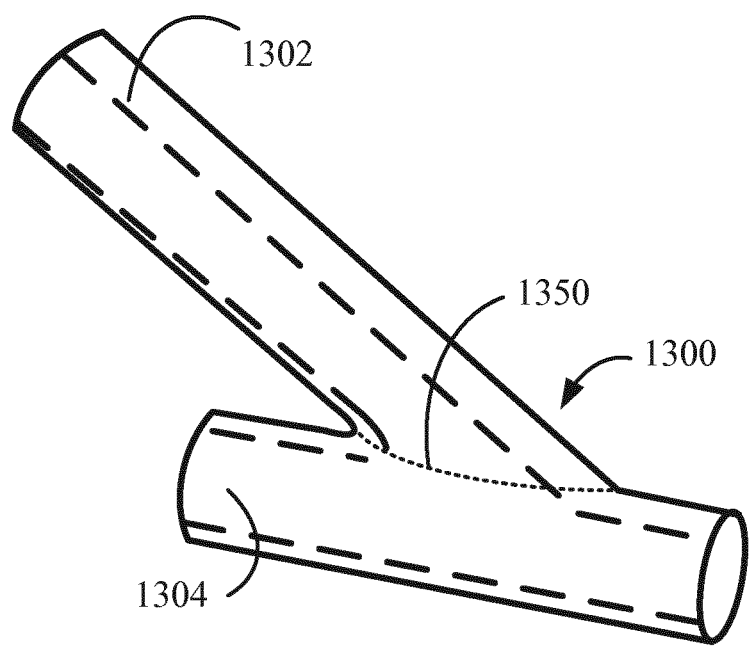
FIGS. 13A and 13B are elevated oblique view simplified illustrations of other exemplary embodiments in accordance with the current method and apparatus.
Figure 13B:
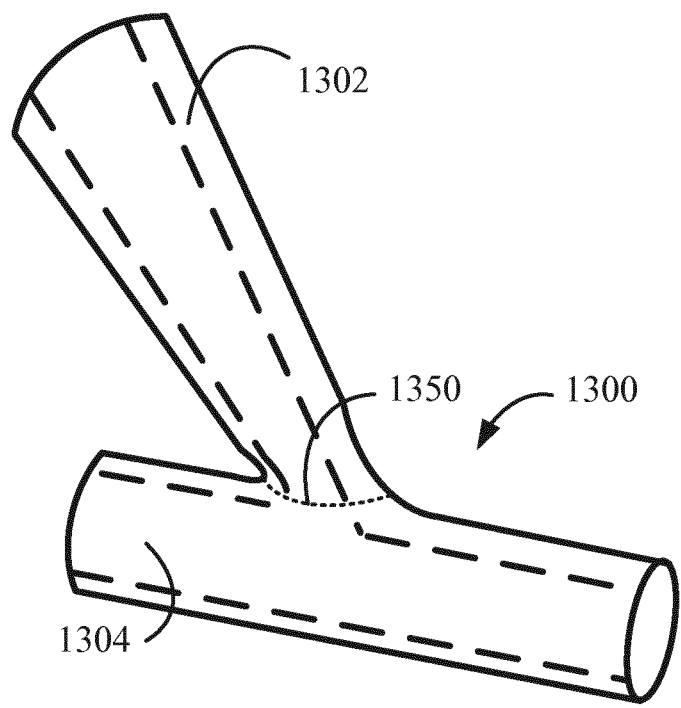

FIGS. 13A and 13B, is an elevated oblique view simplified illustrations of other exemplary embodiments in accordance with the current method and apparatus of the type depicted in FIGS. 7A, 7B, 8A, 8B and 12. In FIG. 12A, support 1300 venous portion 1302 may extend to a greater length measured from anastomosis 1350 depicted in FIGS. 13A and 13B as a dotted line, than support 1300 host artery portion 1304. The length of venous portion 1302 may be in the range between 1 and 8 cm. A length of venous portion 1302 more commonly employed may be in the range between 2 and 6 cm, and a length of venous portion 1302 even more commonly employed may be in the range between 3 and 5 cm.

FIG. 13B depicts a support 1300, similar to that shown in FIG. 13A. In FIG. 13B, venous portion 1302 may be conical in shape, the narrower end closest to anastomosis 1350 and the wider end farthest from anastomosis 1350, allowing for gradual, controlled expansion of a vein (not shown) accommodated inside venous portion 1302 of support 1300 to a vessel diameter acceptable to serve as a vascular access. The distance between anastomosis 1350 and a segment of a vessel having a diameter acceptable to serve as a vascular access (not shown) may be approximately 2-5 cm from anastomosis 1350.

Advantageous vascular support unit thus are provided with a suitable length to allow for an unhindered vascular access.

Figure 14:
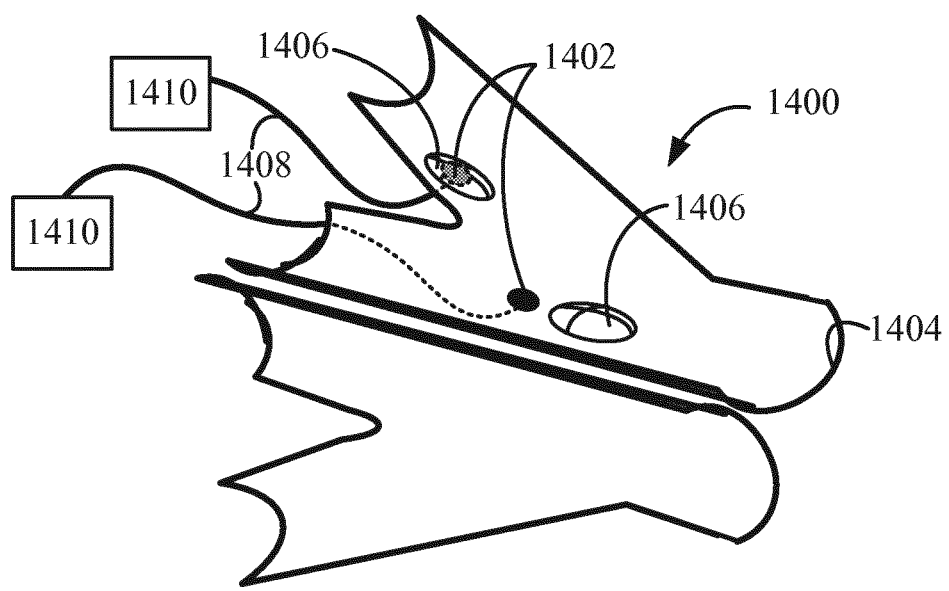
FIG. 14 is an elevated oblique view simplified illustration of yet another exemplary embodiment in accordance with the current method and vascular apparatus.

Reference is now made to FIG. 14, which is an elevated oblique view simplified illustration of still another exemplary embodiment in accordance with the current method and apparatus. Support 1400, of the type shown in FIG. 7A may include one or more sensors 1402 attached to internal wall 1404 of support 1400. Additionally or alternatively, sensors 1402 may attached to or be located inside one or more flow modifying elements 1406. Output signals from sensors 1402 may be carried by a wire 1408 to a controller 1410. Alternatively, output signals may be transmitted from sensors 1402 to a remote receiver in controller 1410.

Sensors 1402 may be one or more sensors selected from a group of sensors consisting of flow meters, pressure sensors, Doppler transducers, NIRS sensors, PH sensors and may provide information regarding flow rate and patterns, blood pressure, degree of stenosis and similar in the vessels accommodated within support 1400.

Information from sensors 1402 may be employed to adjust vascular support 1200 in real time to achieve optimal blood flow conditions through anastomosed vessels (not shown) enclosed within support 1400 or to continuously or periodically monitor maturation of the vascular access over a period of time to enable early diagnosis of impending complications.

Figure 15:
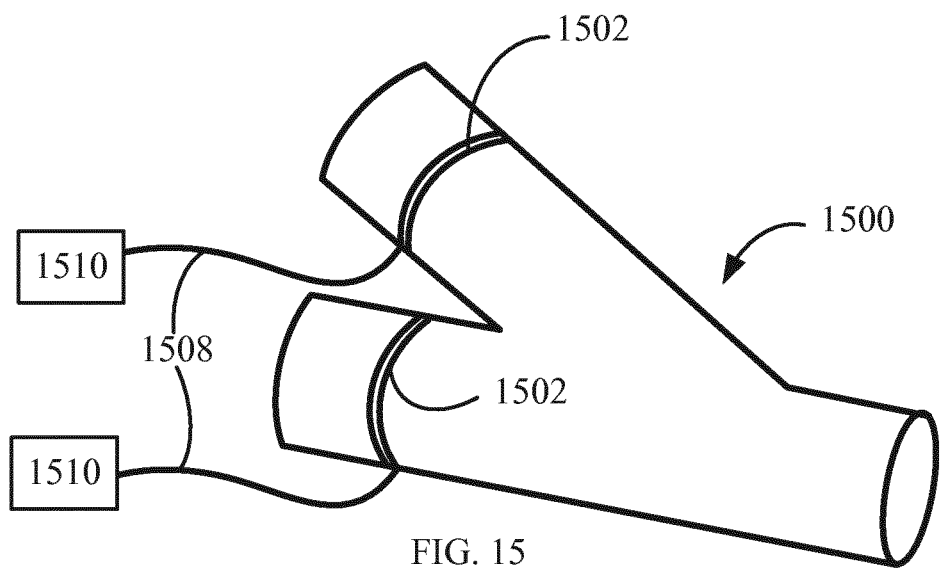
FIG. 15 is an elevated oblique view simplified illustration of still another exemplary embodiment in accordance with the current method and apparatus.

As shown in FIG. 15, which is an elevated oblique view simplified illustration of still another exemplary embodiment in accordance with the current method and apparatus, vascular support 1500, of the type shown in FIG. 7B may include one or more sensors 1502 attached to external wall 1502 of support 1500. Output signals from sensors 1502 may be carried by a wire 1508 to a controller 1510. Alternatively, output signals may be transmitted from sensors 1502 to a remote receiver in controller 1510.

Sensors 1502 may be one or more sensors selected from a group of sensors consisting of flow meters, pressure sensors, Doppler transducers, and may provide information regarding flow rate and patterns, blood pressure, degree of stenosis and similar in the vessels accommodated within support 1500.

Information from sensors 1502 may be employed to adjust vascular support 1500 in real time to achieve optimal blood flow conditions through anastomosed vessels (not shown) enclosed within support 1500 or to continuously or periodically monitor maturation of the vascular access over a period of time to enable early diagnosis of impending complications and intervention and salvage of non-maturing vascular access.

Figure 16:
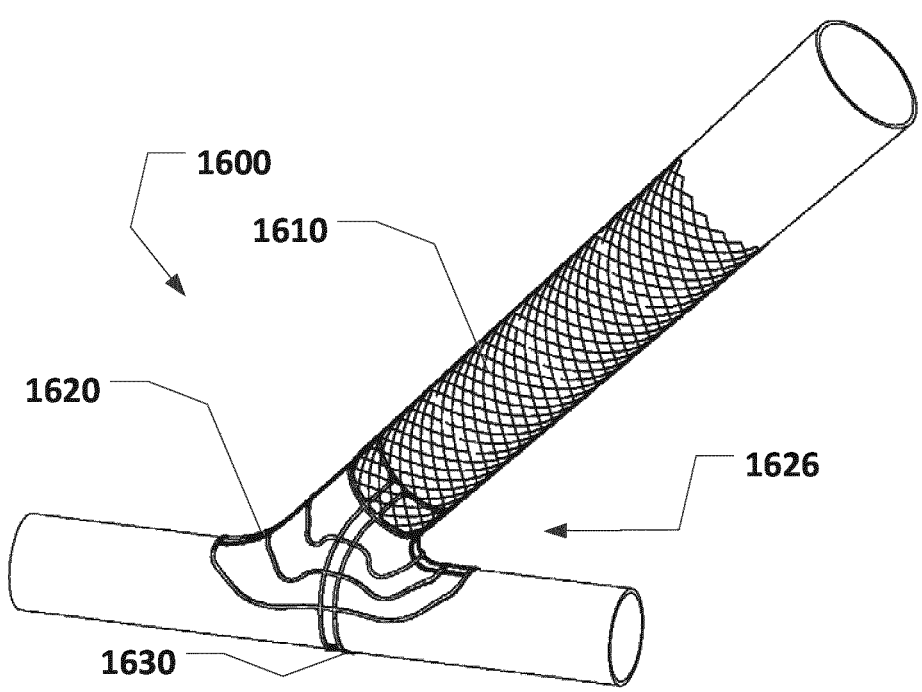
FIG. 16 is an elevated oblique view simplified illustration of yet another exemplary embodiment in accordance with the current method and apparatus.

In some embodiments, the medical device comprises a two-member external support for e.g. end-to-side anastomoses. As shown in FIG. 16, such a two-member external support 1600 may comprise a venous portion, such as a vein restrictor 1610 and an arterial portion, such as a flow adjuster 1620. The vein restrictor 1610 may be connected to the flow adjuster 1620 so that the flow adjuster 1620 is located in-between the vein and the vein restrictor 1610. Alternatively, the vein restrictor 1610 may be connected to the flow adjuster 1620 so that the vein restrictor 1610 is located in-between the vein and the flow adjuster 1620. The connection between the vein restrictor 1610 and the flow adjuster 1620 may be fixed or detachable. If the connection is detachable, then the vein restrictor 1610 can easily be detached from the flow adjuster 1620. The vein restrictor 1610 may be conic, i.e. have a conical shape with a base diameter closer to the end-to-side anastomosed junction than a top diameter and with the top diameter being larger than the base diameter. Moreover, the vein restrictor 1610 may have a length of 5-50 mm, and preferably 10-30 mm, and a top diameter to base diameter ratio of 1.1-1.8 and preferably between 1.3-1.4. Furthermore, the vein restrictor 1610 may be a braided, woven or intertwined mesh. The flow adjuster 1620 may be laser cut and is if used for end-to-side anastomosis, placed at and/or around the junction of the "side portion" (i.e., the arterial member) and the "end portion" (i.e., the venous member). Thus, the flow adjuster 1620 can be designed, constructed, shaped or build to define the angle of anastomosis. Furthermore, the flow adjuster 1620 can be designed, constructed or build to define the base diameter of the vein restrictor 1610. Moreover, the flow adjuster 1620 can be designed, constructed, shaped or build to have a specific rounding 1626 at the side of the end-to-side anastomosed junction having an acute angle. Since the flow adjuster 1620 may be shaped or designed with a rounding 1626, which gives an average Reynolds number smaller than 1,500, turbulent flow may be diminished, minimized or eliminated. Thus, the flow adjuster 1620 may substantially increase laminar flow and contribute to the prevention of vascular access procedure failures. Furthermore, the two-member external support 1600 may comprise an artery brace 1630 for increased support of or for securing the vein restrictor 1610 and/or the flow adjuster 1620.

In some embodiments, at least one flow modifying element is an arterial flow modifying element, i.e. a flow modifying element modifying the flow of an artery.

In some embodiments, the vascular support and/or the flow modifying elements are to be located in the vicinity or the immediate vicinity of an anastomosis, and thus the flow modifying elements will affect and completely eliminate, significantly diminish or at least partially dampen turbulence in the vicinity of the anastomosis. The flow element may include the aforementioned junction rounding.

Although, a flow modifying element has been described herein, the element may instead be a component, i.e. either a separate element or a portion of a different part, such as the vascular support, of the medical device.

It will be appreciated by persons skilled in the art that any of the embodiments and configurations brought forth in this disclosure may also be applicable mutatis mutandis to vessels of the biliary system, urinary system, gastro-intestinal system and other systems where applicable.

It will also be appreciated by persons skilled in the art that the present invention is not limited to what has been particularly shown and described above. Rather, the scope of the invention, as defined by the appended patent claims, includes both combinations and sub-combinations of various features described above as well as modifications and variations thereof which would occur to a person skilled in the art upon reading the foregoing description and which are not in the prior art.

The invention claimed is:

1. An external vascular support for shaping a vein-artery junction between an artery and a vein anastomosed to the artery, the support comprising:
    an arterial portion that is shaped to be in apposition with an exterior wall of the artery when the artery is accommodated within a lumen of the arterial portion; and
    a venous portion that is shaped to be in apposition with an exterior wall of the vein when the vein is accommodated within a lumen of the venous portion; and
    a support junction portion that is defined by a physical connection between the arterial portion and the venous portion, and is shaped to be in apposition with an exterior wall of the vein-artery junction when the vein-artery junction is accommodated within a lumen of the support junction portion;
    wherein said arterial portion and/or said venous portion comprises at least one protrusion configured to press onto the exterior vessel wall of the artery and/or the vein, the protrusion being positioned and dimensioned to reduce turbulence of blood flow inside the artery and/or the vein.

2. The external vascular support of claim 1, wherein the support junction portion is such that, upon implantation of the support, is shaped to maintain the vein at an acute angle to the artery.

3. The external vascular support of claim 2, wherein the at least one protrusion is located on the support junction portion such that, upon implantation of the support, the at least one protrusion is positioned along the venous portion on a side having the acute angle and near the arterial portion.

4. The external vascular support of claim 2, wherein the at least one protrusion is located on the arterial portion such that, upon implantation of the support, the at least one protrusion is positioned along the arterial portion in a region substantially opposite from the junction between the artery and the vein.

5. The external vascular support of claim 4, wherein the at least one protrusion is located closer to a downstream side of the region than an upstream side of the region.

6. The external vascular support of claim 2, wherein the at least one protrusion is located in the support junction portion such that, upon implantation of the support, the at least one protrusion:
    is in apposition with an exterior wall of the vein-artery junction, and;
    imposes a vessel rounding at the vein-artery junction at the acute angle of the junction between the vein and the artery.

7. The external vascular support of claim 6, wherein the vessel rounding has a radius of curvature in the range of 0.25 mm to 4 mm.

8. The external vascular support of claim 7, wherein the vessel rounding has a radius of curvature in the range of 0.5 mm to 2.5 mm.

9. The external vascular support of claim 2, wherein said acute angle is in the range of 20 to 60 degrees.

10. The external vascular support of claim 1, wherein the at least one protrusion is attachable at a desired location on the external vascular support.

11. The external vascular support of claim 1, wherein the at least one protrusion is integral to the external vascular support.

12. The external vascular support of claim 1, wherein the protrusion is expandable.

13. The external vascular support of claim 12, wherein the size and/or shape of the protrusion is adjustable.

14. The external vascular support of claim 1, wherein said venous portion is configured to embrace said vein, and has a truncated conical shape, with a smallest diameter adjacent said junction.

15. The external vascular support of claim 1, wherein said junction is an end-to-side anastomosis of said artery and said vein.

* * * * *

UNITED STATES PATENT AND TRADEMARK OFFICE
CERTIFICATE OF CORRECTION

PATENT NO. : 10,004,508 B2
APPLICATION NO. : 14/236635
DATED : June 26, 2018
INVENTOR(S) : Eyal Orion et al.

Page 1 of 1

It is certified that error appears in the above-identified patent and that said Letters Patent is hereby corrected as shown below:

In the Specification

Column 18, Line 59, "and 412/414 (FIG. 4)" should be removed;

Column 19, Line 44, "8B and 12." should be changed to --8B, 12A and 12B.--;

Column 19, Line 44, "In FIG. 12A," at the end of the line, should be changed to --In FIG. 13A--;

Column 19, Line 46, "FIGS." should be changed to --FIG.--;

Column 19, Line 47, "and 13B" immediately after "13A" should be removed.

Signed and Sealed this
Thirteenth Day of November, 2018

Andrei Iancu
*Director of the United States Patent and Trademark Office*